US008557246B2

(12) United States Patent
Martínez Escribano et al.

(10) Patent No.: US 8,557,246 B2
(45) Date of Patent: Oct. 15, 2013

(54) FUSION PROTEIN THAT DIRECTS VACCINE ANTIGENS TO ANTIGEN-PRESENTING CELLS, AND APPLICATIONS THEREOF

(75) Inventors: José Angel Martínez Escribano, Madrid (ES); Andrés Wigdorovitz, Buenos Aires (AR); Félix Gil Dones, Madrid (ES); Agustin Ostachuk, Buenos Aires (AR); Mariano Pèrez Filguera, Buenos Aires (AR); Javier Dominguez, Madrid (ES); Carmen Núnez Serrano, Madrid (ES); Maria Josè Dus Santos, Buentos Aires (AR); Covadonga Alonso Marti, Madrid (ES)

(73) Assignees: Instituto Nacional de Investigación y Tecnología Agraria y Alimentaria, Madrid (ES); Alternative Gene Expression, S.L., Madrid (ES)

( * ) Notice: Subject to any disclaimer, the term of this patent is extended or adjusted under 35 U.S.C. 154(b) by 387 days.

(21) Appl. No.: 12/922,287

(22) PCT Filed: Mar. 14, 2008

(86) PCT No.: PCT/ES2008/070053
§ 371 (c)(1),
(2), (4) Date: Nov. 19, 2010

(87) PCT Pub. No.: WO2009/112603
PCT Pub. Date: Sep. 17, 2009

(65) Prior Publication Data

US 2011/0061136 A1 Mar. 10, 2011

(51) Int. Cl.

| | |
|---|---|
| ***A01H 5/00*** | (2006.01) |
| ***C12N 5/02*** | (2006.01) |
| ***C12N 15/00*** | (2006.01) |
| ***C12N 1/20*** | (2006.01) |
| ***C07H 21/02*** | (2006.01) |
| ***C07K 14/00*** | (2006.01) |

(52) U.S. Cl.
USPC .................. 424/184.1; 424/192.1; 424/204.1; 424/233.1; 435/325; 435/320.1; 435/252.2; 536/23.4; 530/387.3

(58) Field of Classification Search
None
See application file for complete search history.

(56) References Cited

U.S. PATENT DOCUMENTS

2004/0146948 A1 7/2004 Britton et al.

FOREIGN PATENT DOCUMENTS

ES 2304813 A1 10/2008

OTHER PUBLICATIONS

Ostachuk, Agustin I., et al.; "Expression of ScFv-E2T fusion protein in CHO-K1 cells and alfalfa transgenic plants for the selective directioning to antigen presenting cells," Veterinary Immunology and Immunopathology, 2009, pp. 211-347, vol. 128—Abstract Only.
Bullido, Rosario, et al.; "Characterization of Five Monoclonal Antibodies Specific for Swine Class II Major Histocompatibility Antigens and Crossreactivity Studies With Leukocytes of Domestic Animals," Developmental & Comparative Immunology, 1997, pp. 311-322, vol. 21.
Gil, Felix, et al.; "High-yield expression of a viral peptide vaccine in transgenic plants," Febs Letters, 2001, pp. 13-17, vol. 488.
Ueno, A, et al.; "T-cell immunotherapy for human MK-1-expressing tumors using a fusion protein of the superantigen SEA and anti-MK-1 scFc antibody," Anticancer Research, 2002, pp. 769-776, vol. 22—Abstract Only.
Lopez De Turiso, Jose Angel, et al.; "Recombinant Vaccine for Canine Parvovirus in Dogs," Journal of Virology, 1992, pp. 2748-2753, vol. 66.
International Search Report, Dec. 5, 2008.
Borrego, Belen, et al.; "A DNA vaccine encoding foot-and-mouth disease virus B and T-cell epitopes targeted to class II swine leukocyte antigens protects pigs against viral challenge," Antiviral Research, 2011, pp. 359-363, vol. 93.
Nchinda, Godwin, et al.; "The efficacy of DNA vaccination is enhanced in mice by targeting the encoded protein to dendritic cells, The Journal of Clinical Investigation," 2008, pp. 1427-1436, vol. 118.
Demangel, Carloine, et al.; "Single chain antibody fragments for the selective targeting of antigens to dendritic cells," Molecular Immunology, 2005, pp. 919-985, vol. 42.
Supplemental European Search Report, May 25, 2012.

*Primary Examiner* — Cathy Kingdon Worley
*Assistant Examiner* — Stephen Uyeno
(74) *Attorney, Agent, or Firm* — Tristan A. Fuierer; Andrew D. Gerschultz; Moore & Van Allen, PLLC

(57) ABSTRACT

Fusion protein with directioning of vaccinal antigens toward antigen-presenting cells and the applications thereof. This invention relates to a gene construct that comprises, operatively bound, at least one nucleotide sequence (A) that encodes a polypeptide with SEQ ID NO: 1, which has a region that recognizes the β chain of the class-II DR antigen present on the surface of antigen-presenting cells; and one nucleotide sequence (B) that encodes a vaccinal antigen of interest. Moreover, this invention relates to recombinant vectors useful for the expression of the gene construct of the invention, transgenic cells and plants transformed or transfected with said vectors, fusion proteins encoded by the gene construct of the invention and vaccines that comprise said fusion proteins.

22 Claims, 11 Drawing Sheets

A)

B)

A)

B)

SEQUENCE LISTING

```
<160> NUMBER OF SEQ ID NOS: 23

<210> SEQ ID NO 1
<211> LENGTH: 287
<212> TYPE: PRT
<213> ORGANISM: Artificial Sequence
<220> FEATURE:
<223> OTHER INFORMATION: Synthetic Construct

<400> SEQUENCE: 1

Met Asp Phe Gly Leu Ser Leu Val Phe Leu Ala Leu Ile Leu Lys Gly
1               5                   10                  15

Val Gln Cys Asp Val Gln Leu Val Glu Ser Gly Gly Asp Leu Val Gln
            20                  25                  30

Pro Gly Gly Ser Leu Lys Leu Ser Cys Ala Val Ser Gly Phe Thr Phe
        35                  40                  45

Ser Ser Tyr Gly Met Ser Trp Val Arg Gln Thr Pro Asp Lys Leu Arg
    50                  55                  60

Glu Leu Val Ala Thr Ile Asn Glu Asn Gly Gly Ser Thr Tyr Tyr Pro
65                  70                  75                  80

Asp Ser Val Arg Gly Arg Phe Thr Ile Ser Arg Asp Asn Ala Gln Asn
                85                  90                  95

Thr Leu Tyr Leu Gln Met Ser Ser Leu Lys Ser Glu Asp Thr Ala Met
            100                 105                 110

Tyr Tyr Cys Ala Arg Glu Thr Ser Gly Arg Arg Tyr Trp Phe Tyr Leu
        115                 120                 125

Asp Val Trp Gly Ala Gly Thr Thr Val Thr Val Ser Ser Gly Gly Gly
    130                 135                 140

Gly Ser Gly Gly Gly Gly Ser Gly Gly Gly Gly Ser Gln Ile Val Leu
145                 150                 155                 160

Ser Gln Ser Pro Ala Ile Met Ser Ala Phe Pro Gly Glu Arg Val Thr
                165                 170                 175

Met Thr Cys Ser Ala Ser Ser Ser Val Ser Tyr Met Phe Trp Tyr Gln
            180                 185                 190

Gln Lys Pro Gly Ser Ser Pro Arg Leu Leu Ile Tyr Asp Thr Ser Asn
        195                 200                 205

Leu Ala Ser Gly Val Pro Val Arg Phe Ser Gly Ser Gly Ser Gly Thr
    210                 215                 220

Ser Tyr Ser Leu Thr Ile Ser Arg Met Glu Ala Glu Asp Ala Ala Thr
225                 230                 235                 240

Phe Tyr Cys Gln Gln Trp Phe Ser Tyr Pro Pro Thr Phe Gly Gly Gly
                245                 250                 255
```

```
Thr Lys Val Glu Ile Lys Arg Leu Glu Met Ser Asp Gly Ala Val Gln
            260                 265                 270

Pro Asp Gly Gly Gln Pro Ala Val Arg Asn Glu Arg Ala Thr Gly
        275                 280                 285


<210> SEQ ID NO 2
<211> LENGTH: 4
<212> TYPE: PRT
<213> ORGANISM: Artificial Sequence
<220> FEATURE:
<223> OTHER INFORMATION: Synthetic Construct

<400> SEQUENCE: 2

Gly Ser Pro Gly
1


<210> SEQ ID NO 3
<211> LENGTH: 8
<212> TYPE: PRT
<213> ORGANISM: Artificial Sequence
<220> FEATURE:
<223> OTHER INFORMATION: Synthetic Construct

<400> SEQUENCE: 3

Gly Ser Gly Ser Gly Ser Gly Ser
1               5


<210> SEQ ID NO 4
<211> LENGTH: 21
<212> TYPE: DNA
<213> ORGANISM: Artificial Sequence
<220> FEATURE:
<223> OTHER INFORMATION: Synthetic Construct

<400> SEQUENCE: 4

ctcgagatgt ctgatggagc a                                            21


<210> SEQ ID NO 5
<211> LENGTH: 24
<212> TYPE: DNA
<213> ORGANISM: Artificial Sequence
<220> FEATURE:
<223> OTHER INFORMATION: Synthetic Construct

<400> SEQUENCE: 5

cccgggtcat cctgtagctc tctc                                         24


<210> SEQ ID NO 6
<211> LENGTH: 34
<212> TYPE: DNA
<213> ORGANISM: Artificial Sequence
<220> FEATURE:
<223> OTHER INFORMATION: Synthetic Construct

<400> SEQUENCE: 6

ggtctagaca ccatggactt cgggttgagc ttgg                              34


<210> SEQ ID NO 7
<211> LENGTH: 52
<212> TYPE: DNA
<213> ORGANISM: Artificial Sequence
<220> FEATURE:
<223> OTHER INFORMATION: Synthetic Construct

<400> SEQUENCE: 7

cctccagaac ctccgcctcc tgatccgcca cctcctgagg agacggtgac cg          52
```

<210> SEQ ID NO 8
<211> LENGTH: 52
<212> TYPE: DNA
<213> ORGANISM: Artificial Sequence
<220> FEATURE:
<223> OTHER INFORMATION: Synthetic Construct

<400> SEQUENCE: 8
caggaggcgg aggttctgga ggaggtggga gtcaaattgt tctctcccag tc 52

<210> SEQ ID NO 9
<211> LENGTH: 38
<212> TYPE: DNA
<213> ORGANISM: Artificial Sequence
<220> FEATURE:
<223> OTHER INFORMATION: Synthetic Construct

<400> SEQUENCE: 9
cccggggtcg acctcgagcc gtttgatctc caccttgg 38

<210> SEQ ID NO 10
<211> LENGTH: 44
<212> TYPE: DNA
<213> ORGANISM: Artificial Sequence
<220> FEATURE:
<223> OTHER INFORMATION: Synthetic Construct

<400> SEQUENCE: 10
ggggatatcc accatggaga tgcgagctgt ggtcaatcgc tctt 44

<210> SEQ ID NO 11
<211> LENGTH: 42
<212> TYPE: DNA
<213> ORGANISM: Artificial Sequence
<220> FEATURE:
<223> OTHER INFORMATION: Synthetic Construct

<400> SEQUENCE: 11
ggggatatcc accatgagac ttcgggtctg agcttgggtt tt 42

<210> SEQ ID NO 12
<211> LENGTH: 38
<212> TYPE: DNA
<213> ORGANISM: Artificial Sequence
<220> FEATURE:
<223> OTHER INFORMATION: Synthetic Construct

<400> SEQUENCE: 12
ggggatatcc accatggctg tcttggggct gctcttct 38

<210> SEQ ID NO 13
<211> LENGTH: 42
<212> TYPE: DNA
<213> ORGANISM: Artificial Sequence
<220> FEATURE:
<223> OTHER INFORMATION: Synthetic Construct

<400> SEQUENCE: 13
aggtctagaa ctctccacac acaggagagc cagtggatag ac 42

<210> SEQ ID NO 14
<211> LENGTH: 38
<212> TYPE: DNA
<213> ORGANISM: Artificial Sequence
<220> FEATURE:
<223> OTHER INFORMATION: Synthetic Construct

<400> SEQUENCE: 14
ggggatatcc accatggaga cagacacact cctgctat 38

<210> SEQ ID NO 15
<211> LENGTH: 42
<212> TYPE: DNA
<213> ORGANISM: Artificial Sequence
<220> FEATURE:
<223> OTHER INFORMATION: Synthetic Construct

<400> SEQUENCE: 15
ggggatatcc accatggtcc ccatgactca gcttctcttg gt 42

<210> SEQ ID NO 16
<211> LENGTH: 44
<212> TYPE: DNA
<213> ORGANISM: Artificial Sequence
<220> FEATURE:
<223> OTHER INFORMATION: Synthetic Construct

<400> SEQUENCE: 16
ggggatatcc accatggagt acacagttac tcaggtcttt gata 44

<210> SEQ ID NO 17
<211> LENGTH: 39
<212> TYPE: DNA
<213> ORGANISM: Artificial Sequence
<220> FEATURE:
<223> OTHER INFORMATION: Synthetic Construct

<400> SEQUENCE: 17
ggggatatcc accatggatt ttcaagtgca gattttcag 39

<210> SEQ ID NO 18
<211> LENGTH: 30
<212> TYPE: DNA
<213> ORGANISM: Artificial Sequence
<220> FEATURE:
<223> OTHER INFORMATION: Synthetic Construct

<400> SEQUENCE: 18
gggtctagaa ctggatggtg ggaagatgga 30

<210> SEQ ID NO 19
<211> LENGTH: 28
<212> TYPE: DNA
<213> ORGANISM: Artificial Sequence
<220> FEATURE:
<223> OTHER INFORMATION: Synthetic Construct

<400> SEQUENCE: 19
gcccgggatg gacttcgggt tgagcttg 28

<210> SEQ ID NO 20
<211> LENGTH: 46
<212> TYPE: DNA
<213> ORGANISM: Artificial Sequence
<220> FEATURE:
<223> OTHER INFORMATION: Synthetic Construct

<400> SEQUENCE: 20
cactagttta atgatgatga tgatgatgct cagcgaagta atcccg 46

<210> SEQ ID NO 21
<211> LENGTH: 21
<212> TYPE: PRT

-continued

<213> ORGANISM: canine parvovirus

<400> SEQUENCE: 21

Ser Asp Gly Ala Val Gln Pro Asp Gly Gly Gln Pro Ala Val Arg Asn
1 5 10 15

Glu Arg Ala Thr Gly
20

<210> SEQ ID NO 22
<211> LENGTH: 614
<212> TYPE: PRT
<213> ORGANISM: Artificial Sequence
<220> FEATURE:
<223> OTHER INFORMATION: Synthetic Construct

<400> SEQUENCE: 22

Met Asp Phe Gly Leu Ser Leu Val Phe Leu Ala Leu Ile Leu Lys Gly
1 5 10 15

Val Gln Cys Asp Val Gln Leu Val Glu Ser Gly Gly Asp Leu Val Gln
20 25 30

Pro Gly Gly Ser Leu Lys Leu Ser Cys Ala Val Ser Gly Phe Thr Phe
35 40 45

Ser Ser Tyr Gly Met Ser Trp Val Arg Gln Thr Pro Asp Lys Arg Leu
50 55 60

Glu Leu Val Ala Thr Ile Asn Glu Asn Gly Gly Ser Thr Tyr Tyr Pro
65 70 75 80

Asp Ser Val Arg Gly Arg Phe Thr Ile Ser Arg Asp Asn Ala Gln Asn
85 90 95

Thr Leu Tyr Leu Gln Met Ser Ser Leu Lys Ser Glu Asp Thr Ala Met
100 105 110

Tyr Tyr Cys Ala Arg Glu Thr Ser Gly Arg Arg Tyr Trp Phe Tyr Leu
115 120 125

Asp Val Trp Gly Ala Gly Thr Thr Val Thr Val Ser Ser Gly Gly Gly
130 135 140

Gly Ser Gly Gly Gly Gly Ser Gly Gly Gly Gly Ser Gln Ile Val Leu
145 150 155 160

Ser Gln Ser Pro Ala Ile Met Ser Ala Phe Pro Gly Glu Arg Val Thr
165 170 175

Met Thr Cys Ser Ala Ser Ser Ser Val Ser Tyr Met Phe Trp Tyr Gln
180 185 190

Gln Lys Pro Gly Ser Ser Pro Arg Leu Leu Ile Tyr Asp Thr Ser Asn
195 200 205

Leu Ala Ser Gly Val Pro Val Arg Phe Ser Gly Ser Gly Ser Gly Thr
210 215 220

Ser Tyr Ser Leu Thr Ile Ser Arg Met Glu Ala Glu Asp Ala Ala Thr
225 230 235 240

Phe Tyr Cys Gln Gln Trp Phe Ser Tyr Pro Pro Thr Phe Gly Gly Gly
245 250 255

Thr Lys Val Glu Ile Lys Arg Leu Glu His Leu Asp Cys Lys Pro Glu
260 265 270

Phe Ser Tyr Ala Ile Ala Lys Asp Glu Arg Ile Gly Gln Leu Gly Ala
275 280 285

Glu Gly Leu Thr Thr Thr Trp Lys Glu Tyr Ser Pro Gly Met Lys Leu
290 295 300

Glu Asp Thr Met Val Ile Ala Trp Cys Glu Asp Gly Lys Leu Met Tyr
305 310 315 320

-continued

```
Leu Gln Arg Cys Thr Arg Glu Thr Arg Tyr Leu Ala Ile Leu His Thr
                325                 330                 335

Arg Ala Leu Pro Thr Ser Val Val Phe Lys Lys Leu Phe Asp Gly Arg
            340                 345                 350

Lys Gln Glu Asp Val Val Glu Met Asn Asp Asn Phe Glu Phe Gly Leu
        355                 360                 365

Cys Pro Cys Asp Ala Lys Pro Ile Val Arg Gly Lys Phe Asn Thr Thr
    370                 375                 380

Leu Leu Asn Gly Pro Ala Phe Gln Met Val Cys Pro Ile Gly Trp Thr
385                 390                 395                 400

Gly Thr Val Ser Cys Thr Ser Phe Asn Met Asp Thr Leu Ala Thr Thr
                405                 410                 415

Val Val Arg Thr Tyr Arg Arg Ser Lys Pro Phe Pro His Arg Gln Gly
            420                 425                 430

Cys Ile Thr Gln Lys Asn Leu Gly Glu Asp Leu His Asn Cys Ile Leu
        435                 440                 445

Gly Gly Asn Trp Thr Cys Val Pro Gly Asp Gln Leu Leu Tyr Lys Gly
    450                 455                 460

Gly Ser Ile Glu Ser Cys Lys Trp Cys Gly Tyr Gln Phe Lys Glu Ser
465                 470                 475                 480

Glu Gly Leu Pro His Tyr Pro Ile Gly Lys Cys Lys Leu Glu Asn Glu
                485                 490                 495

Thr Gly Tyr Arg Leu Val Asp Ser Thr Ser Cys Asn Arg Glu Gly Val
            500                 505                 510

Ala Ile Val Pro Gln Gly Thr Leu Lys Cys Lys Ile Gly Lys Thr Thr
        515                 520                 525

Val Gln Val Ile Ala Met Asp Thr Lys Leu Gly Pro Met Pro Cys Arg
    530                 535                 540

Pro Tyr Glu Ile Ile Ser Ser Glu Gly Pro Val Glu Lys Thr Ala Cys
545                 550                 555                 560

Thr Phe Asn Tyr Thr Lys Thr Leu Lys Asn Lys Tyr Phe Glu Pro Arg
                565                 570                 575

Asp Ser Tyr Phe Gln Gln Tyr Met Leu Lys Gly Glu Tyr Gln Tyr Trp
            580                 585                 590

Phe Asp Leu Glu Val Thr Asp His His Arg Asp Tyr Phe Ala Glu His
        595                 600                 605

His His His His His His
    610


<210> SEQ ID NO 23
<211> LENGTH: 342
<212> TYPE: PRT
<213> ORGANISM: Bovine viral diarrhoea virus

<400> SEQUENCE: 23

His Leu Asp Cys Lys Pro Glu Phe Ser Tyr Ala Ile Ala Lys Asp Glu
1               5                   10                  15

Arg Ile Gly Gln Leu Gly Ala Glu Gly Leu Thr Thr Thr Trp Lys Glu
            20                  25                  30

Tyr Ser Pro Gly Met Lys Leu Glu Asp Thr Met Val Ile Ala Trp Cys
        35                  40                  45

Glu Asp Gly Lys Leu Met Tyr Leu Gln Arg Cys Thr Arg Glu Thr Arg
    50                  55                  60

Tyr Leu Ala Ile Leu His Thr Arg Ala Leu Pro Thr Ser Val Val Phe
65                  70                  75                  80
```

-continued

```
Lys Lys Leu Phe Asp Gly Arg Lys Gln Glu Asp Val Val Glu Met Asn
                85                  90                  95

Asp Asn Phe Glu Phe Gly Leu Cys Pro Cys Asp Ala Lys Pro Ile Val
            100                 105                 110

Arg Gly Lys Phe Asn Thr Thr Leu Leu Asn Gly Pro Ala Phe Gln Met
        115                 120                 125

Val Cys Pro Ile Gly Trp Thr Gly Thr Val Ser Cys Thr Ser Phe Asn
    130                 135                 140

Met Asp Thr Leu Ala Thr Thr Val Val Arg Thr Tyr Arg Arg Ser Lys
145                 150                 155                 160

Pro Phe Pro His Arg Gln Gly Cys Ile Thr Gln Lys Asn Leu Gly Glu
                165                 170                 175

Asp Leu His Asn Cys Ile Leu Gly Gly Asn Trp Thr Cys Val Pro Gly
            180                 185                 190

Asp Gln Leu Leu Tyr Lys Gly Gly Ser Ile Glu Ser Cys Lys Trp Cys
        195                 200                 205

Gly Tyr Gln Phe Lys Glu Ser Glu Gly Leu Pro His Tyr Pro Ile Gly
    210                 215                 220

Lys Cys Lys Leu Glu Asn Glu Thr Gly Tyr Arg Leu Val Asp Ser Thr
225                 230                 235                 240

Ser Cys Asn Arg Glu Gly Val Ala Ile Val Pro Gln Gly Thr Leu Lys
                245                 250                 255

Cys Lys Ile Gly Lys Thr Thr Val Gln Val Ile Ala Met Asp Thr Lys
            260                 265                 270

Leu Gly Pro Met Pro Cys Arg Pro Tyr Glu Ile Ile Ser Ser Glu Gly
        275                 280                 285

Pro Val Glu Lys Thr Ala Cys Thr Phe Asn Tyr Thr Lys Thr Leu Lys
    290                 295                 300

Asn Lys Tyr Phe Glu Pro Arg Asp Ser Tyr Phe Gln Gln Tyr Met Leu
305                 310                 315                 320

Lys Gly Glu Tyr Gln Tyr Trp Phe Asp Leu Glu Val Thr Asp His His
                325                 330                 335

Arg Asp Tyr Phe Ala Glu
            340
```

FUSION PROTEIN THAT DIRECTS VACCINE ANTIGENS TO ANTIGEN-PRESENTING CELLS, AND APPLICATIONS THEREOF

CROSS-REFERENCE TO RELATED APPLICATIONS

This application is filed under the provisions of 35 U.S.C. §371 and claims the priority of International Patent Application No. PCT/ES2008/070053 filed on 14 Mar. 2008 entitled "Fusion Protein that Directs Vaccine Antigens to Antigen-Presenting Cells, and Applications Thereof" in the name of José Angel Martínez Escribano, et al., which is hereby incorporated by reference herein in its entirety.

TECHNICAL FIELD OF THE INVENTION

This invention relates to a method of directioning vaccinal antigens toward antigen-presenting cells, based on the synthesis of a fusion protein which comprises: a polypeptide that has a region that recognises an epitope present on the surface of an antigen-presenting cell, and another polypeptide which is the vaccinal antigen of interest.

BACKGROUND OF THE INVENTION

The obtainment of recombinant products of vaccinal interest in different expression systems, such as bacteria, fungi, yeasts, plants, insect cells and larvae, mammalian cells, etc., has been known for some time. Amongst these systems, plants offer numerous advantages as compared to other expression systems, since, in general, they represent an economical, safe and easy-to-obtain method of obtaining proteins of potential pharmaceutical interest, for example, recombinant subunit vaccines, without the need for costly fermentation systems.

However, in all systems, the main limitation in the obtainment of vaccines from recombinant subunits of the pathogen is the low immunogenicity of the recombinant products obtained; as a result, very high, repeated vaccine doses are usually required to equal the immune response obtained with the conventional immunogen (complete deactivated pathogen). This circumstance makes the production costs of recombinant subunit vaccines very high as compared to conventional vaccines and, therefore, many of them do not currently reach the market.

Different alternatives have been followed in order to improve the immunogenicity of recombinant subunit vaccines. One of them is based on the use of CTLA4- and L-selectin-type molecules to direct vaccinal antigens toward antigen-presenting cells in mice [Boyle J. S. et al., Enhanced responses to a DNA vaccine encoding a fusion antigen that is directed to sites of immune induction. Nature. 1998, Mar. 26; 392 (6674): 408-411]. However, these strategies have not proven to be equally effective in species other than the murine species, which makes it necessary to search for other alternatives based on the directioning of vaccinal antigens toward the cells in charge of antigen presentation in other species, particularly the human species.

BRIEF DESCRIPTION OF THE INVENTION

The invention relates to a method, alternative to those present in the state of the art, which increases the effectiveness of recombinant subunit vaccines when these are applied to different species, both animals in general, and humans in particular. Using the method of the invention based on the directioning of antigens toward their presenting cells, it was possible to enhance the host-mediated immune response whilst reducing the dose of vaccine applied, equaling or exceeding the immune response achieved by the application of conventional vaccines.

Therefore, the system for the directioning of vaccinal antigens toward antigen-presenting cells proposed by this invention is composed of a fusion protein that comprises at least one polypeptide (A) which has a region that recognises an epitope present on the surface of an antigen-presenting cell, and another polypeptide (B), the vaccinal antigen of interest, which is responsible for triggering the immune response in the host.

In a particular embodiment of the invention, polypeptide (A) comprises a region that recognises the β chain of the Class-II DR antigen (Region D). Said polypeptide is a single-chain (scFv) recombinant APCH1 ("Antigen Presenting Cells Homing 1") antibody, characterised by SEQ ID NO: 1, derived from monoclonal antibody 1F12. Thus, polypeptide (A) is formed by the variable region of the heavy chain (VH) of monoclonal antibody 1F12 fused, through a flexible peptide, to the variable region of the light chain (VL) of monoclonal antibody 1F12. Monoclonal antibody 1F12 recognises the β chain of the Class-II DR antigen in a large number of species; consequently, it would be applicable to multiple species, including humans.

In another particular embodiment of the invention, peptide (B) (vaccinal antigen of interest) is the vaccine peptide against canine parvovirus (CPV) called 2L21 (SEQ ID NO: 21), protein E2T (SEQ ID NO: 23) or E2 from the bovine viral diarrhoea virus, protein VP60 from the rabbit haemorrhagic disease virus, protein VP6 from the rotavirus or the haemagglutinin protein from the influenza virus.

2L21 is formed by two antigenic subsites distant from the amino-terminal region of protein VP2 from the CPV capsid and was previously published as the first synthetic vaccine peptide (López de Turiso, J. A., Cortés, E., Martínez, C., Ruiz de Ybánez, R., Simarro, I., Vela, C., Casal, I. (1992) J. Virol. 66:2 748-2753). Peptide 2L21, fused to APCH1, has been expressed in plants. Furthermore, said peptide 2L21 has been expressed unfused in plants, or fused to an irrelevant protein from the immunogenic standpoint (β-glucuronidase, GUS), the expression whereof had been successfully performed prior to this in the inventors' laboratory (Gil F., Brun A., Wigdorovitz A., Martínez-Torrecuadra J. L., Catalá R., Casal I., Salinas J., Borca M. V. and Escribano J. M. FEBS Letters 488: 13-17, 2001). Fusion protein 2L21-GUS is a very stable protein, with a low degradation rate and perfectly adapted to expression in plants.

Therefore, the invention presents a method of directioning vaccinal antigens toward the presenting cells thereof, composed of a fusion protein, such as, for example, APCH1-2L21 or APCH1-E2T, which comprises APCH1 fused to vaccine peptide 2L21 or E2T, respectively. As explained below, fusion protein APCH1-2L21 was expressed in plants, leading to transgenic *Arabidposis thaliana* plants, and fusion protein APCH1-E2T was expressed in mammalian cells.

Moreover, it was proven that fusion protein APCH1-2L21 maintained the antigenic and immunogenic characteristics of peptide 2L21, inducing high titles of specific antibodies in groups of animals immunised by oral route as well as intraperitoneal, intravenous, intramuscular or subcutaneous route, it being much greater than that induced by synthetic peptide 2L21 alone or fused to GUS (2L21-GUS). These results showed that fusion protein APCH1-2L21 enhances the immune response in animals, which confirms the hypothesis of an increase in the immunogenicity of a vaccinal antigen through the directioning thereof toward antigen-presenting cells by means of a polypeptide with a region (A) that recognises an epitope present on the surface of an antigen-presenting cell.

The system of directioning vaccinal antigens provided by this invention exhibits numerous advantages, since it makes it possible to direct the fused vaccinal antigen toward antigen-presenting cells, thereby facilitating capture of the vaccinal antigen and enhancing the immune response. This reduces the dose of recombinant subunit vaccine from the pathogen to be administered in order to obtain an immune response equal to or greater than that obtained with conventional vaccines from intact pathogen, in both animals and humans.

DESCRIPTION OF THE FIGURES

FIG. 1A: schematically shows the gene expression construct that is integrated in the nuclear genome of *Arabidopsis thaliana*, which comprises the nucleotide sequence of APCH1, led by the 35S constitutive promoter of the cauliflower mosaic virus (CaMV 35S) [LB: left edge; RB: right edge; APCH1-Peptide 2L21: fusion that encodes fusion protein APCH1-2L21; NOS-Ter: polyadenylation sequence under the control of the nopaline synthase promoter (NOS-Pro); NPT II (Kan R): kanamycin resistance gene.

FIG. 1B: shows the expected three-dimensional structure for fusion protein APCH1-2L21, obtained from "Swiss-protein", where the two independently folded globular domains (VH and VL) may be observed.

FIG. 2A: shows the results of a Northern blot analysis of the transcription of the fusion gene (APCH1-2L21) in transgenic *A. thaliana* plants, over 5 μg of total RNA per plant line, hybridised using the complete DNA sequence of the APCH1-2L21 fusion labelled with $^{32}P$ as the probe.

FIG. 2B: shows the results of a Western blot analysis of the protein extracts (40 μg of total soluble protein) extracted from fresh leaves of the different transgenic lines of *A. thaliana* analysed by Northern blot.

Panel I: (a) macrophages incubated with plant extracts (negative control); (b) labelling of the macrophages' cellular surface obtained with antibody 1F12; (c) labelling obtained with the extract of total soluble protein, which contained fusion protein APCH1-2L21.

Panel II: low-magnification detail of cells incubated with control extract (1), antibody 1F12 (2) and plant extract that expresses fusion protein APCH1-2L21 (3). (b and c) detail at higher magnifications of the cellular labelling obtained with monoclonal antibody 1F12 and with fusion protein APCH1-2L21, respectively.

Figure 4:
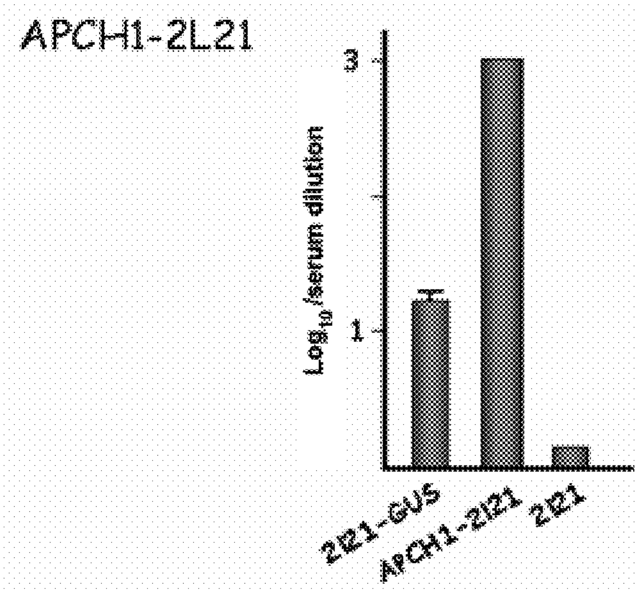

FIG. 4 bar diagram that shows the result of the analysis of the immune response obtained with various preparations of peptide 2L21 from CPV, specifically, the specific antibody immune response obtained in mice by immunising with peptide 2L21 by itself (2L21), fused to antibody APCH1 (APCH1-2L21) or fused to the 13-GUS (2L21-GUS) protein.

Figure 5:
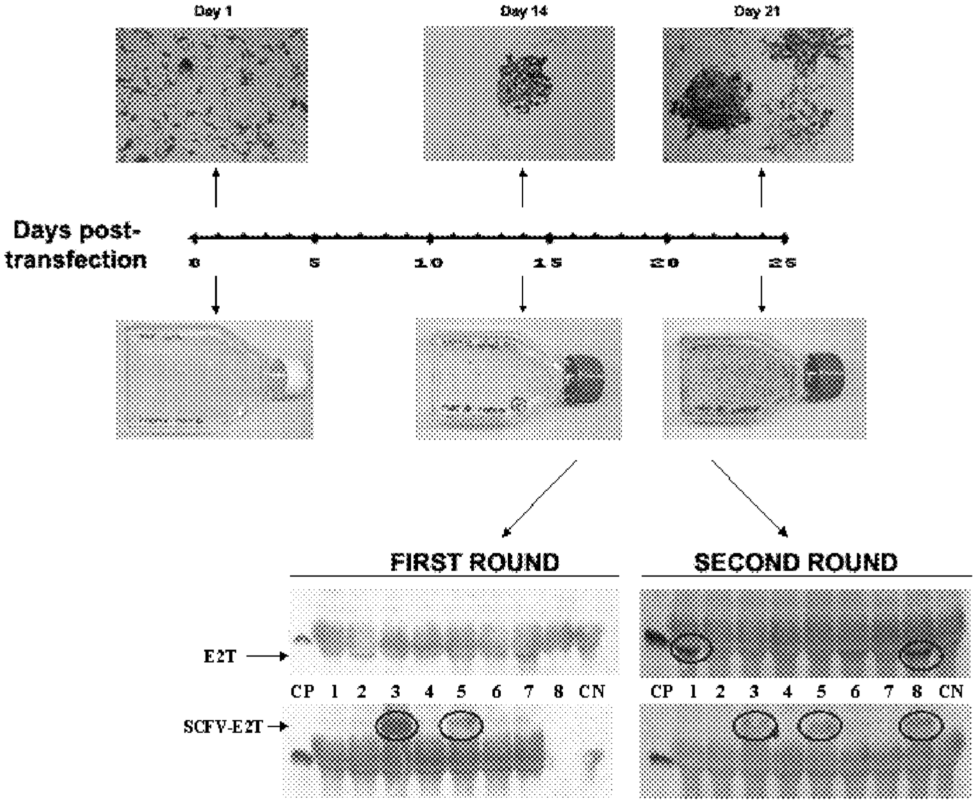

FIG. 5 production of the stable lines of CHOK1 (mammalian ovarian cells) that express APCH1-E2T and E2T. A more detailed explanation of this figure may be found in point 2.4 of Example 2.

Figure 6:
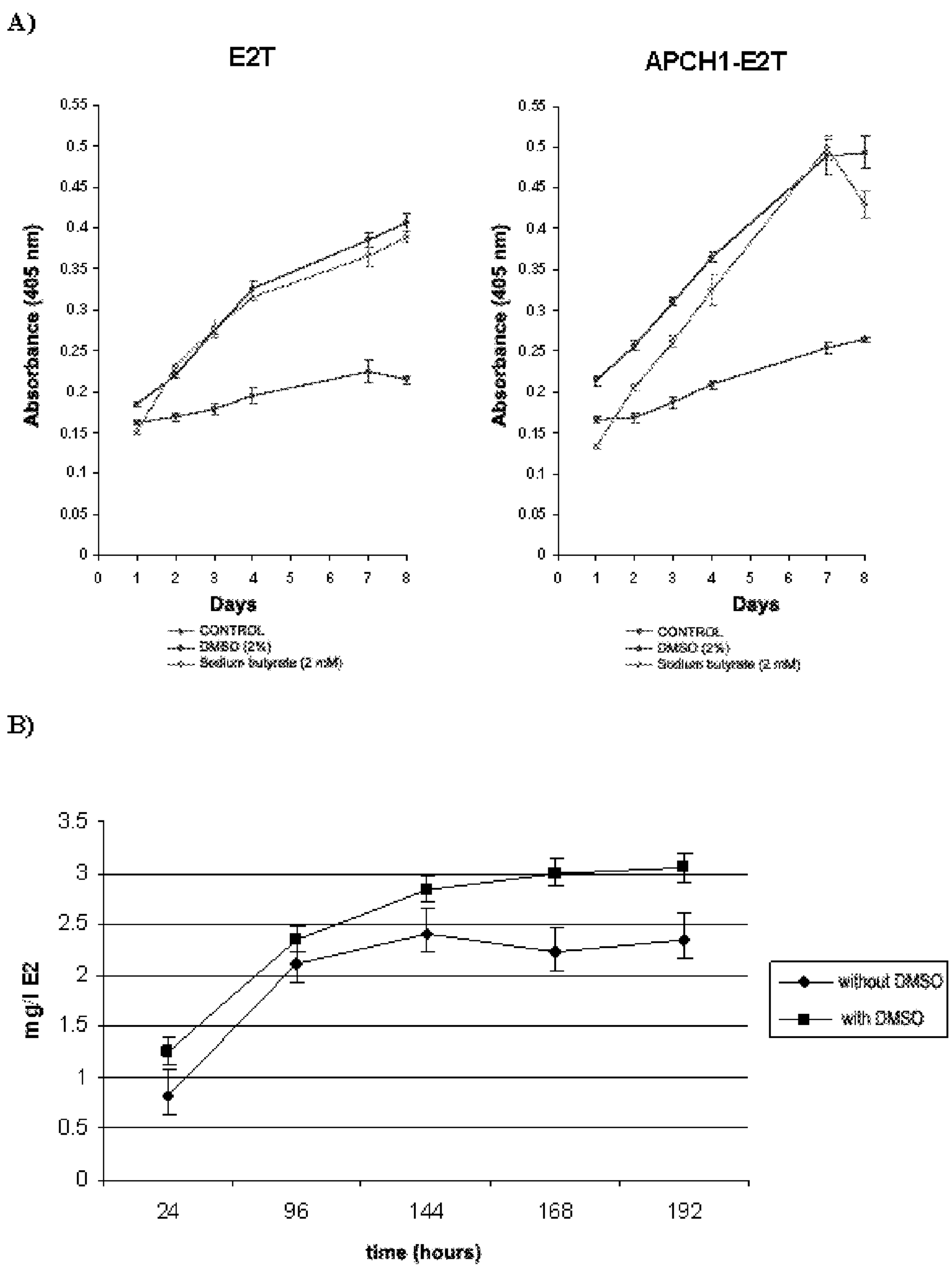

FIG. 6 evaluation of the production of recombinant proteins in the supernatant of the cell lines developed. The assays were performed in duplicate for each of the groups, in culture flasks (T75), with and without DMSO, and in bottles (rollers), with and without DMSO. In the case of T75 at time 0, 3×106 cells were seeded, whereas the rollers were initiated with 16×106 cells, such that the ratio of cells per volume between both was maintained. 1 ml was extracted every 24 h and they were preserved at −20° C. until the ELISA was performed. A more detailed explanation of this figure may be found in point 2.8 of Example 2.

FIG. 6A: cell lines grown in tissue culture flasks (T75).

FIG. 6B: cell lines grown in "roller" bottles.

Figure 7:
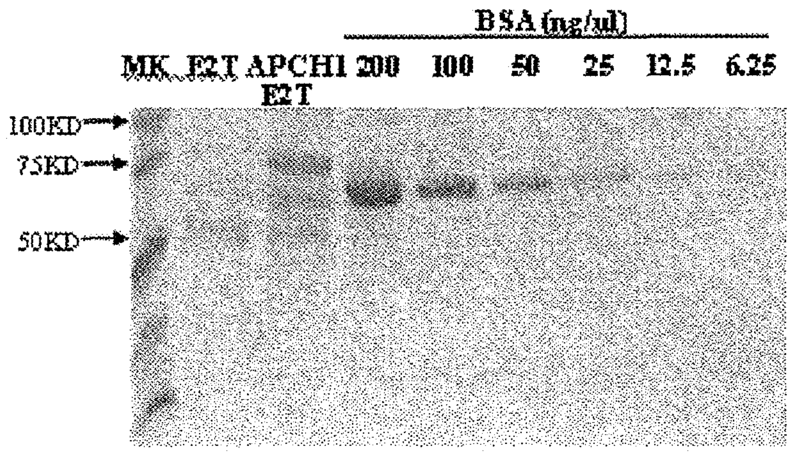
Figure 7:
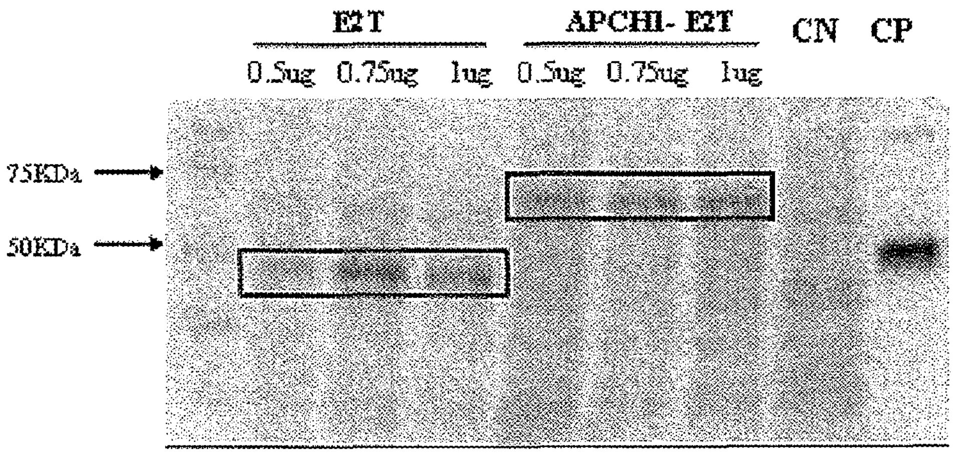

FIG. 7 staining with Coomassie and Western Blot of APCH1-E2T and E2T. A more detailed explanation of this figure may be found in point 2.9 of Example 2.

Figure 8:
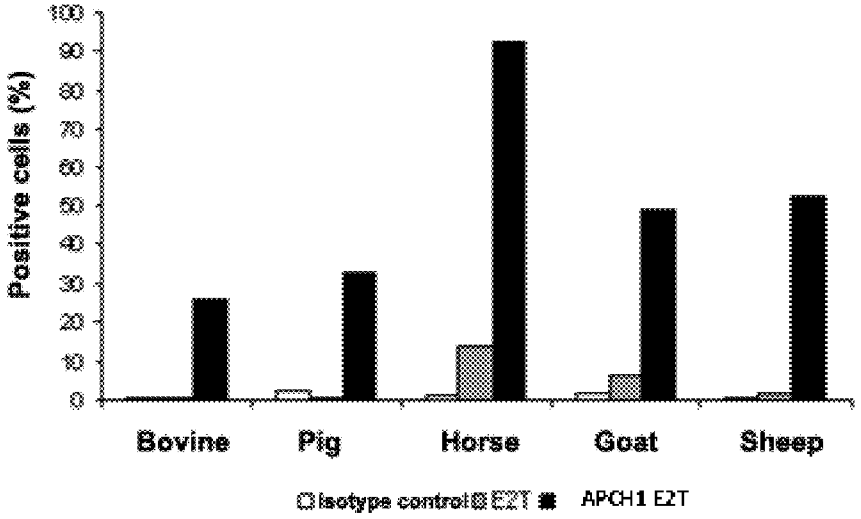

FIG. 8 recognition of APCH1-E2T to MHCII (major histocompatibility complex) of mononuclear cells. MHCII is a family of genes that encodes certain plasma membrane glycoproteins involved in the mechanisms of antigen presentation and processing to T lymphocytes, as well as cytokines and complement system proteins, which are relevant in the immunological response.

Figure 9:
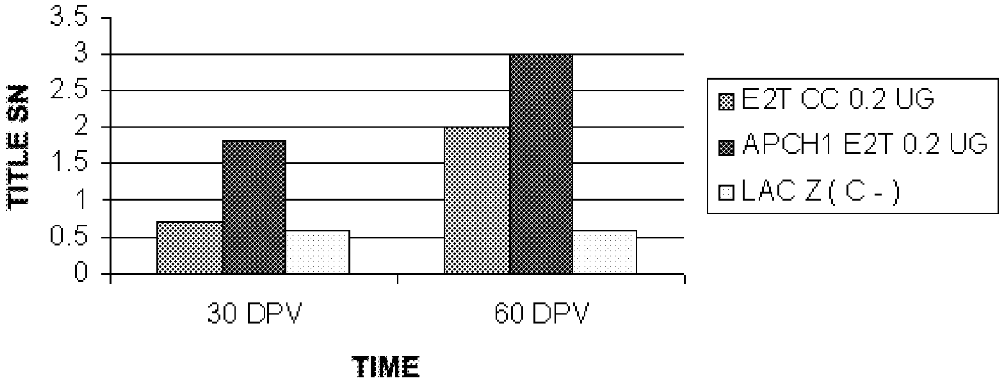

FIG. 9 immune response in guinea pigs immunised with the experimental molecule. The Lac-z gene encodes β-galactosidase, an enzyme that converts lactose into glucose and galactose, and was used as a negative control. The DPV term located in the figure refers to days post-vaccination.

Figure 10:
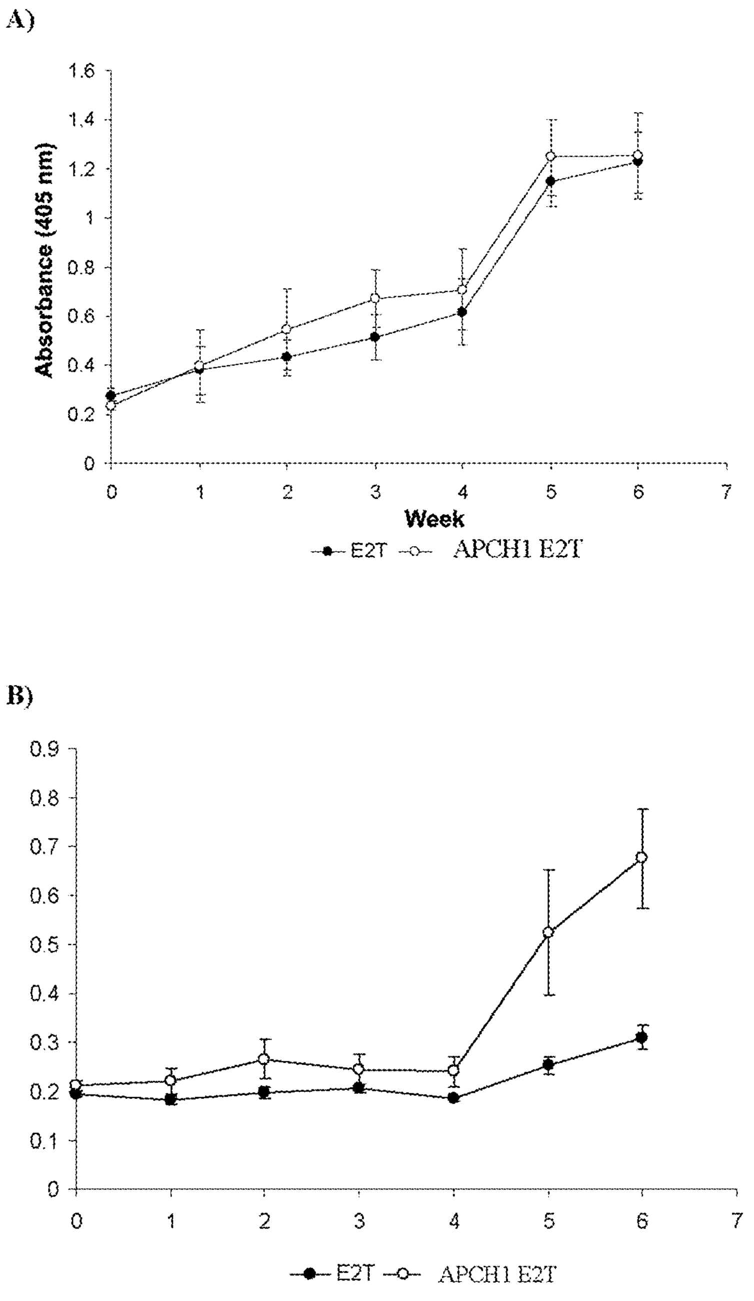

FIG. 10 immune response in bovines immunised with culture supernatants that express protein APCH1-E2T and E2T.

FIG. 10A: bovines immunised with 1 μg of APCH1-E2T or E2T.

FIG. 10B: bovines immunised with 0.2 μg of APCH1-E2T or E2T.

Figure 11:
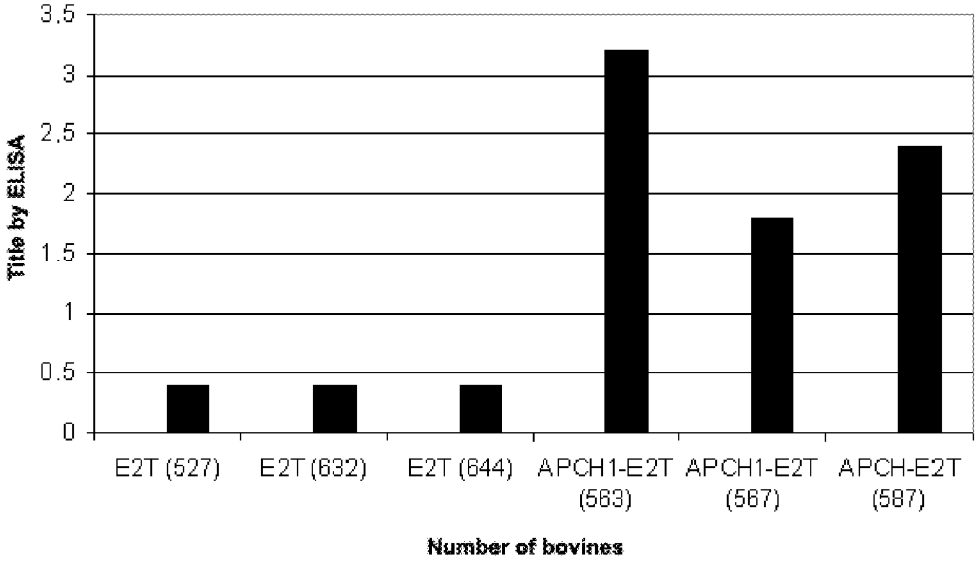

FIG. 11 title of antibodies in bovines vaccinated with 0.2 μg of APCH1-E2T or E2T.

DETAILED DESCRIPTION OF THE INVENTION

The invention relates to a DNA construct, hereinafter DNA construct of the invention, which comprises, operatively bound, directly or indirectly, at least:

a) one nucleic acid sequence (A) that encodes a polypeptide which comprises a region that recognises an epitope present on the surface of an antigen-presenting cell; and
b) one nucleic acid sequence (B) that comprises the nucleotide sequence which encodes the vaccinal antigen of interest, responsible for triggering the immune response in the host.

Nucleic acid sequence (A) encodes a polypeptide which comprises a region that recognises an epitope present on the surface of an antigen-presenting cell. Practically any polypeptide which comprises a region that recognises an epitope present on the surface of an antigen-presenting cell may be used in this invention, such as, for example, a monoclonal antibody, or a fragment thereof, in its single-chain (scFv), bi-functional (diabody) or complete (Fab+Fc) forms. However, in a particular embodiment of the invention, nucleic acid sequence (A) encodes an APCH1 polypeptide (SEQ ID NO: 1) which comprises a region that recognises an epitope (chain β) of the Class-II DR antigen. Class II is expressed in immune system cells as surface polypeptides and comprises the HLAD antigens (human leukocyte antigen D), sub-classified into DR (DRA and DRB), DQ and DP. Said polypeptide is a single-chain recombinant antibody, derived from monoclonal antibody 1F12, composed of the variable region of the heavy chain (VH) of monoclonal antibody 1F12 fused, through a flexible peptide (linker or hinge), to the variable region of the light chain (VL) of monoclonal antibody 1F12. The 3'-end of the VL-encoding sequence is bound to the 5'-end of the encoding sequence for said linker and the 3'-end of the nucleotide sequence encoding said linker is bound to the 5'-end of the VL-encoding sequence. scFv APCH1 was designed in such a way that one or more restriction sequences could be added at the 3'-end of VL in order to be able to perform different fusions with the antigens to be assayed, and it contains a restriction sequence (XbaI) at the 5'-end of VH, which made it possible to easily obtain fusions from the plasmid where they are located and carry them to the plant transformation plasmids.

Monoclonal antibody 1F12 recognises the β chain of the Class-II DR antigen in a large number of animal species and, therefore, may be applied to multiple species, including humans. Due to its properties, said antibody, in any of its forms (scFv, bi-functional or complete), may direct a vaccine peptide fused thereto toward the antigen-presenting cells that exhibit this type of molecules on the surface, thereby facilitating capture of the antigen and enhancing the response, since most of the protein expressed would reach its destination prior to being degraded. Thus, it is possible to compensate for the low accumulation levels of xenoproteins (recombinant subunit vaccines of the pathogen) presented by transgenic plants or animals, or compensate for production costs in other systems.

Nucleic acid sequence (B) encodes a vaccinal antigen of interest which may be practically any peptide or protein, regardless of the origin thereof (eukaryotic, prokaryotic, viral, etc.), susceptible to being expressed in recombinant form and to inducing an immune response in the host, whether an animal in general or human beings in particular. Below, we present a number of examples that may act as vaccinal antigens of interest: peptide 2L21 from CPV, protein VP60 from the rabbit haemorrhagic disease virus (RHDV), protein VP6 from rotavirus, protein E2 or E2T from the bovine viral diarrhoea virus, a vaccinal antigen against tumours and tumoural cells, etc.

In a preferred embodiment, nucleic acid sequence (A) is not directly fused to nucleic acid sequence (B), but, instead, it is advantageous to introduce a spacer peptide (linker) between the 3'-end of nucleic acid sequence (A) and the 5'-end of nucleic acid sequence (B). Therefore, if so desired, the DNA construct of the invention may additionally contain a nucleic acid sequence (C) which contains the nucleotide sequence that encodes a spacer peptide located between said nucleic acid sequences (A) and (B), where the 5'-end of said nucleic acid sequence (C) is bound to the 3'-end of said nucleic acid sequence (A) and the 3'-end of said nucleic acid sequence (C) is bound to the 5'-end of said nucleic acid sequence (B). Advantageously, said spacer peptide (C) is a peptide with structural flexibility. Practically any peptide with structural flexibility may be used. For illustrative purposes, said flexible peptide may contain repeats of amino acid residues, in particular Gly and Ser residues, or any other adequate repeat of amino acid residues. In a particular embodiment, said flexible spacer peptide is selected from sequence SEQ ID NO: 2 or SEQ ID NO: 3.

In order to facilitate the isolation and purification of the fusion peptide or protein obtained by means of this invention, the DNA construct of the invention may contain, if so desired, a nucleic acid sequence that encodes a peptide susceptible to being used for the purpose of isolating or purifying the fusion peptide or protein. Therefore, in a particular embodiment, the DNA construct of the invention includes, if so desired, a nucleic acid sequence (D) which contains the nucleotide sequence that encodes a peptide susceptible to being used for isolation or purification purposes. Said nucleic acid sequence (D) may be located in any position that does not alter the functionality of the polypeptide which comprises the region that recognises an epitope present on the surface of an antigen-presenting cell or the polypeptide of interest. For illustrative purposes, said nucleic acid sequence (D) may be located downstream from the 3'-end of said nucleic acid sequence (B).

Practically any peptide or peptide sequence that allows for the isolation or purification of the fusion peptide or protein may be used; for example, polyhistidine sequences, peptide sequences susceptible to being recognised by monoclonal antibodies that may serve to purify the resulting fusion protein by immunoaffinity chromatography, such as tag peptides, etc.; for example, epitopes derived from the haemagglutinin protein of the flu virus or the C-myc epitope, etc.

The DNA construct of the invention may be obtained using techniques that are widely known in the state of the art [Sambrook et al., "Molecular cloning, a Laboratory Manual", 2$^{nd}$ ed., Cold Spring Harbor Laboratory Press, N.Y., 1989, Vol. 1-3]. Said DNA construct of the invention may incorporate, operatively bound, an expression-regulating sequence of the nucleotide sequence that encodes the product or products of interest, constituting a gene expression construct. As used in this description, the expression "operatively bound" means that the product or products of interest is (are) expressed within the correct reading frame under the control of the expression-regulating or control sequences.

Therefore, in a preferred embodiment, the gene construct of the invention comprises, operatively bound, an expression control sequence of the nucleotide sequence that encodes the fusion protein of the invention. Control sequences are sequences that control and regulate the transcription and, if applicable, the translation of said fusion protein, and include promoter sequences, sequences encoding transcriptional regulators, ribosome-binding sequences (RBS) and/or transcription termination sequences. In a particular embodiment, said expression control sequence is functional in prokaryotic cells and organisms, for example, bacteria, etc., whereas, in another particular embodiment, said expression control sequence is functional in eukaryotic cells and organisms, for example, insect cells, vegetable cells, mammalian cells, etc. Illustrative examples of promoters that may be present in the gene expression construct provided by this invention include the CaMV 35S promoter for plants, the polyhedrin promoter or the p10 protein for the baculovirus system, the early cytomegalovirus promoter for DNA vaccines, the synthetic early/late poxvirus promoter, etc.

Advantageously, said gene expression construct additionally comprises a marker or gene that encodes a motif or a phenotype which allows for the selection of the host cell transformed by said gene expression construct. Illustrative examples of said markers that could be present in the gene expression construct of the invention include antibiotic resistance genes, genes conferring resistance to toxic compounds, and, in general, all those that make it possible to select the genetically transformed plants.

The DNA construct of the invention, or the gene expression construct provided by this invention, may be inserted in an appropriate vector. Therefore, another aspect of the invention relates to a vector, such as an expression vector, that comprises said DNA construct. The choice of the vector will depend on the host cell wherein it will be subsequently introduced. For illustrative purposes, the vector wherein said DNA sequence is introduced may be a plasmid or a vector which, when introduced into a host cell, is integrated into the genome of said cell or not. Said vector may be obtained by conventional methods known by those skilled in the art [Sambrook et al., 1989, cited supra]. In a particular embodiment, said recombinant vector is a vector that is useful to transform or be inserted into plant cells or animal cells. Thus, the vector of the invention may be, for example, *Agrobacterium tumefaciens* or a viral vector capable of infecting and being expressed in animal cells (such as, for example, mammalian or insects cells) or plant cells. In a particular embodiment of the invention, the viral vector used is *Baculovirus.*

Said vector may be used to transform, transfect or infect cells susceptible to being transformed, transfected or infected thereby. Consequently, another aspect of the invention relates to a cell infected with a viral vector provided by this invention. In a particular embodiment, said infected cell is a vegetable cell infected with an appropriate viral vector, said infected vegetable cell being capable of expressing the fusion protein provided by this invention. Vegetable cells infected with recombinant viral vectors may be obtained following infection of a plant with said recombinant viral vector. Thus, plant infectious viral vectors may be used for the expression of epitopes of animal pathogens or tumoural cells in plants, in order to produce edible vaccines against said pathogens or tumoural cells.

Additionally, the recombinant vectors provided by this invention may be used to transform or transfect eukaryotic or prokaryotic cells. Therefore, another aspect of the invention relates to a transformed or transfected cell that comprises said recombinant vector, or said DNA construct provided by this invention, or said gene expression construct provided by the invention. Transformed or transfected cells may be obtained by conventional methods known by those skilled in the art [Sambrook et al., 1989, cited supra].

In a particular embodiment, said recombinant vector is a viral vector. The recombinant vectors of the invention are capable of infecting and being expressed in plant cells, algae cells or animal cells, preferably in insect cells or insect larvae cells.

Consequently, another aspect of the invention relates to a transformed or transfected cell that comprises, at least, a DNA construct of the invention, or a recombinant vector provided by this invention, or a gene expression construct provided by this invention.

Another aspect of the invention relates to a transgenic cell that comprises, inserted in its genome, at least one DNA construct of the invention. In a particular embodiment, said transgenic cell comes from a vegetable cell and comprises, inserted in its genome or in the genome of a chloroplast, at least one DNA construct of the invention. Transgenic plants may be obtained from said transgenic vegetable cells or from transgenic vegetable material. Therefore, another aspect of the invention relates to a transgenic plant that comprises, at least, one vegetable transgenic cell provided by this invention. As is well known, a potentially interesting application of transgenic plants is the expression of proteins or epitopes of animal pathogens or of tumoural cells in plants, in order to produce edible vaccines against said pathogens or tumoural cells.

In another particular embodiment of the invention, said transgenic cell is an animal cell, preferably from a mammal or an insect, and, more preferably, from an insect larva. Therefore, the invention also relates to a transgenic non-human animal, particularly a transgenic mammal, insect or insect larva that expresses the peptide or protein of interest with a high yield.

The DNA construct of the invention may be used to produce fusion proteins described in this invention. Therefore, another aspect of the invention relates to a method of producing said fusion protein, which comprises growing a cell or organism provided by this invention under conditions that allow for the production of said fusion protein. The conditions to optimise the culturing of said cell or organism will depend on the cell or organism used. If so desired, the method of producing a product of interest provided by this invention additionally includes the isolation and purification of said fusion protein.

Another aspect of the invention also provides a method of expressing a gene that encodes a fusion protein provided by this invention in a plant, which comprises transforming said plant with, at least, one DNA construct provided by this invention. The transformation of cells from vegetable tissues may be performed by conventional methods. For a review of gene transfer to plants, including vectors, DNA transfer methods, etc., see, for example, the book titled "Ingeniería genética y transferencia génica" [Genetic Engineering and Gene Transfer], by Marta Izquierdo, Ed. Pirámide (1999), in particular chapter 9, titled "Gene transfer to plants", pages 283-316.

Another aspect of the invention relates to a fusion protein that may be obtained by the expression of the nucleic acid sequence contained in the DNA construct provided by this invention. More specifically, the invention provides a fusion protein that comprises:

(A) a polypeptide with a region that recognises an epitope present on the surface of an antigen-presenting cell, and
(B) a vaccinal antigen of interest.

In a particular embodiment, the invention provides a fusion protein that comprises:

(A) a polypeptide selected from the group formed by intact monoclonal antibody 1F12, a fragment of monoclonal antibody 1F12 which contains the region that recognises the β chain of the Class-II DR antigen, monoclonal antibody 1F12 in bi-functional form and a recombinant scFv that contains the variable region of the heavy chain (VH) of monoclonal antibody 1F12 fused, through a flexible peptide, to the variable region of the light chain (VL) of monoclonal antibody 1F12 (APCH1); and
(B) a vaccinal antigen of interest.

The fusion protein provided by this invention may additionally contain, if so desired, a spacer peptide between the polypeptide that comprises a region which recognises an epitope present on the surface of an antigen-presenting cell and the polypeptide of interest; and/or a peptide designed to facilitate the isolation or purification of the fusion protein.

In general, the fusion protein provided by this invention, in particular when the polypeptide that comprises the region which recognises an epitope present on the surface of an antigen-presenting cell is an scFv, is a relatively small molecule and, in general, maintains the binding specificity of the original antibody wherefrom the polypeptide that comprises the region which recognises an epitope present on the surface of an antigen-presenting cell is derived, and does not require the complex assembly process for the complete antibody. On the other hand, due to their small size, they have greater tissue penetrability.

Another aspect of the invention relates to a recombinant vaccine that comprises the fusion protein provided by this invention and, optionally, a pharmaceutically acceptable excipient.

The assays performed (see examples) show that the fusion protein provided by this invention enhances the immune response in animals, since it induces titles of antibodies that are much greater than those obtained with the vaccine peptide by itself or fused to an irrelevant protein, thereby confirming the hypothesis of an increase in the immunogenicity of a vaccine peptide through the directioning thereof toward antigen-presenting cells by means of a polypeptide that comprises a region which recognises an epitope present on the surface of an antigen-presenting cell, such as scFv APCH1.

Therefore, since it directs the fused vaccinal antigen toward the antigen-presenting cells that exhibit the corresponding epitope on the surface thereof, the system of directioning vaccinal antigens provided by this invention facilitates capture of the vaccinal antigen and the immune response is enhanced, as most of the protein expressed reaches its destination prior to becoming degraded; furthermore, this prevents the vaccinal antigen from being eliminated from the blood stream before it is processed by the cells in charge of presenting it to the immune system and, therefore, generating a protective immune response. Thanks to the directioning of the vaccinal antigen toward antigen-presenting cells, a large part thereof is correctly presented to the immune system; the result is a potent immune response which, depending on the particular case, will be, at least, 50 times that obtained by the vaccinal antigen by itself (in terms of the title of specific antibodies). Therefore, this invention immununologically improves the recombinant subunit vaccines produced in any system.

Deposit of Biological Material

Plasmid pBIAPCH1-2L21: was deposited at the Spanish Type Culture Collection (CECT), Burjassot, Valencia, on Dec. 12, 2003, being assigned accession number CECT: 5857, in accordance with the Budapest Treaty.

Plasmid pcDNAAPCH1-E2T: was deposited at the Spanish Type Culture Collection (CECT), Burjassot, Valencia, on May 3, 2008, being assigned accession number CECT: 7387, in accordance with the Budapest Treaty.

The examples presented below serve to illustrate the invention and should not be considered to limit the scope thereof.

EXAMPLES

Example 1

Directioning of Vaccinal Antigens Toward Antigen-Presenting Cells in Order to Enhance the Immune Response in Animals. Fusion of the Single-Chain Recombinant Antibody APCH1 (SEQ ID NO: 1) to Peptide 2L21 and the Expression Thereof in Transgenic Plants 1.1 Vegetable Material The model plant used was *Arabidopsis thaliana*, ecotype Columbia. The genus *Arabidopsis* belongs to the family Cruciferae (Brassicaceae or Cruciferae).

1.2 Bacterial Strains Used 1.2.1 *Escherichia coli*

Strains DH5-α and TOP-10 of *Escherichia coli* (Clontech), which exhibit the following characteristics, were used for the transformation and growth of the plasmids:

| Bacterial strain | Genotype | Remarkable utilities |
|---|---|---|
| DH5-α | supE44 hsd R17 recA1 endA1 gyrA96 thi-1 relA1 | Deficient strain in recombination, used for plating and growth of plasmids |
| TOP-10 | $F^-$ mcr A Δ(mrr-hsd RMS-mcrBC) | Competent strain, very efficient in transformation with linkages. |

1.2.2 *Agrobacterium tumefaciens*

Strains C58C1 and AGLO 5-α of *Agrobacterium tumefaciens* (Hellens R. and Mullineaux P. A guide to *Agrobacterium* binary Ti vectors. Trends in Plant Science 5: 446-451, 2000) were used for the infiltration of *A. thaliana* flowers.

1.3 Plasmids Used 1.3.1 Commercial Plasmids

In order to obtain the different constructs that express the different peptides assayed, various commercial plasmids were used. Plasmid pGEM-Teasy was used for the cloning and sequencing of PCR products, whereas binary plasmid PBI-121 and derivatives thereof were used in the transformation of *Agrobacterium* and in the subsequent infiltration of *A. thaliana* plants.

pGEM-Teasy (Promega): This plasmid is especially designed for the cloning and sequencing of PCR products. It contains a region with multiple restriction sites (polylinker). The polylinker has been previously digested with EcoRV and, subsequently, 3'-thymidines were added at both ends in order to facilitate cloning of the PCR products. Moreover, it makes it possible to select the recombinants by means of the LacZ gene.

pBI-121 (Clontech Cat. 6018-1): It is derived from plasmid pBI-101. It contains the 35S promoter of the cauliflower mosaic virus (CaMV 35S) and directs the expression of the GUS gene and a 260-bp (base pairs) fragment which contains the polyadenylation sequence of the nopaline synthase (NOS-ter) gene of plasmid Ti of *Agrobacterium*. It also contains an RK2 replication origin (with a low number of copies) and a kanamycin resistance gene (Npt2).

Also used, in addition to these commercial plasmids, was plasmid p35S-TEV (4,051 bp), generated at Dr. Escribano's laboratory (National Institute for Agricultural Research [INIA]) and derived from plasmid pBI121 [Dr. Escribano's laboratory collection (INIA)], which contains the 35S promoter of the cauliflower mosaic virus (CaMV 35S), the transcription-enhancing sequence (TEV) of the tobacco mottling virus, whereafter a multiple cloning region and the Vsp polyadenylation signal appear. This plasmid was re-used in the sub-cloning of some constructs as a previous step to the cloning thereof in the binary plasmid. These two plasmids are available to the public at the inventors' laboratory and are not a part of the invention claimed.

1.3.2 Plant Transformation Plasmids Developed During the Implementation of This Invention For the embodiment of this example, the plasmid identified as pBI APCH1-2L21 was generated, which was used in the genetic transformation of plants. The antigen expressed in said plasmid pBI APCH1-2L21 is the fusion of APCH1 to peptide 2L21 from canine parvovirus (CPV).

The sequences that encode said antigen and the respective fusions thereof were obtained by means of PCR amplification. 2 types of commercial polymerases were used, ECO-TAQ (Ecogen), which was primarily used in the colony analyses, and Pow DNA-polymerase (Roche), which exhibits a corrective activity and was used to amplify the transgene sequences. The primers used are shown in Table 1. Positions 1-6 of SEQ ID NO: 4; 1-6 of SEQ ID NO: 5; 2-7 of SEQ ID NO: 6 and 1-18 of SEQ ID NO: 9 are restriction targets. Positions 1-35 of SEQ ID NO: 7 and positions 1-32 of SEQ ID NO: 8 represent the artificial flexible sequence that serves for binding in scFv (APCH1).

TABLE 1

| Primers used | |
|---|---|
| Name of the primer | 5'-3' sequence |
| 2L21 XhoI | SEQ ID NO: 4 |
| 2L21 SmaI | SEQ ID NO: 5 |
| 5' VH XbaI | SEQ ID NO: 6 |
| 3' VH linker | SEQ ID NO: 7 |
| 5' VL linker | SEQ ID NO: 8 |
| 3' VL | SEQ ID NO: 9 |

1.4 Antibodies

In order to detect the different recombinant antigens produced in plants, different commercial mouse monoclonal antibodies and rabbit polyclonal antibodies, and the respective secondary antibodies conjugated to alkaline phosphatase (AP) and/or peroxidase (HRP), were used.

TABLE 2

| Monoclonal antibody (mouse) | Specificity | Use | Supplier |
|---|---|---|---|
| 3C9 | anti-2L21 CPV | WB/ELISA | Ingenasa |
| Polyclonal antibody (rabbit) | Specificity | Use | Supplier |
| IgG | anti-β-Glucuronidase | WB/ELISA | Molecular probes |
| Secondary antibodies-conjugated | | Supplier | |
| Anti-mouse conjugated with AP | | Biorad | |
| Anti-mouse conjugated with HRP | | Amersham | |

*WB: Western Blot 1.5 Hybridoma 1F12

In order to develop the scFv identified as APCH1, we started from hybridoma 1F12, provided by Dr. Javier Domínguez (Dept. of Biotechnology, INIA), which expresses the 1F12 monoclonal antibody that recognises the β chain of the Class-II DR antigen. Hybridoma 1F12 was kept under culture in RPMI-1640 medium (Biowhittaker), supplemented with 0.01 mM pyruvic acid (Sigma), 2 mM L-glutamine (Sigma), 100 U/ml penicillin and 20 μg/ml gentamycin sulfate (Biowhittaker). Hybridoma 1F12 is available to the public at the INIA laboratories and is not a part of the invention claimed.

1.6 Commercial ELISAS

INGEZIM PARVO CANINO 1.5.CPV.K.1 (Ingenasa), indirect-type immunoenzymatic assay for the detection and quantification of specific antibodies against canine parvovirus in dog sera.

1.7 Growth of *Arabidopsis thaliana*

The model plant used was *Arabidopsis thaliana*, ecotype Columbia. The genus *Arabidopsis* belongs to the family Cruciferae (Brassicaceae or Cruciferae).

1.7.1 On Soil

In order to grow *Arabidopsis* plants in soil, the seeds were planted on the surface, in flowerpots or plastic cells containing a mixture of universal substrate and vermiculite (3:1). The mixture was previously soaked in distilled water and autoclave-sterilised at 101 kPa (1 atm) of pressure for 20 minutes at 120° C. The flowerpots or cells were placed in trays which were subsequently covered with plastic in order to maintain an adequate humidity and prevent contaminations during germination. The trays were kept in the dark at 4° C. for 48 hours, in order to favour homogeneous germination of the seeds. Subsequently, the trays were taken to culture chambers at 22° C., with a photoperiod of 16 hours of fluorescent light and 8 hours in the dark. One week after planting, the plastic was removed, always keeping the tray with water. The plants were watered once a week with universal minimal medium (Haughn and Somerville, (1986), Sulfonylurea resistant mutants of *Arabidopsis thaliana*. Molec. General Genetics 204: 430-434). The plants were kept under these conditions until flowering began (6-7 weeks), which is the ideal time for infiltration. Occasionally, in order to improve the infiltration yields, some flowers are cut until the secondary inflorescences, which are more numerous, develop.

1.7.2 In Petri Dishes

For germination of the seeds in plates, MS medium (Murashige T. and F. Skoog. A revised medium for rapid growth and bioassays with tobacco tissue cultures. Physiol. Plant. 15: 473-497, 1962), supplemented with 1% sucrose and solidified with 0.8% agar, and the corresponding antibiotic were used. The seeds were sterilised for 10 minutes in a solution of 30% sodium hypochlorite and 0.01% Triton X-100, and subsequently washed 5 times in sterile water. The seeds were seeded on the Petri dishes, which were taken to 4° C. in the dark for 48 hours. Subsequently, they were taken to culture chambers under conditions of 22° C. and 16 hours of light followed by 8 hours in the dark. After two weeks, the seedlings were transplanted to soil and grown under the conditions described above.

1.8 Bacterial Culture Media and Obtainment of Competent Cells

The cultures of *E. coli* were performed in LB medium (Sigma) in the presence of the corresponding selective agent (Sambrook et al., 1989) for 14-16 hours at 37° C. The preparation of competent cells was performed using the rubidium chloride method, described by Hanahan (Studies on transformation of *E. coli* with plasmids. J. Mol. Biol. 166: 557-580. 1983).

The cultures of the different strains of *Agrobacterium* were performed in liquid LB or in plates, supplemented with 50 μg/ml of kanamycin and 50 μg/ml of rifampycin (Sambrook et al., 1989), and kept at 28° C. for 36-48 hours.

Long-term preservation of the bacterial cultures was performed in dimethylsulfoxide (DMSO) at a final concentration of 6% at −80° C. (Sambrook et al., 1989).

1.9 Bacterial Transformation Methods 1.9.1 Transformation of *E. Coli*

Strains DH5-α and TOP-10 were used to maintain the plasmids and generate new ones. Both competent strains were transformed following Birnboim and Dolly's protocol (Birnboin H. C. and Dolly J. A rapid alkaline extraction procedure for screening recombinant plasmid DNA. Nucl. Acid Res. 7: 1513-1516. 1979). Briefly, the plasmid DNA or linkage product was added to a 100-μl aliquot of thawed competent cells and kept at 4° C. for 30 minutes. Subsequently, a thermal shock at 42° C. was caused, which increases pore permeability, 600 μl of LB were added and they were incubated at 37° C., under stirring, for 1-1.5 hours. The bacterial cells were sedimented by centrifugation at 3,500 rpm for 3 minutes and plated in a solid medium whereto the necessary selection antibiotics had been previously added. The plates were incubated in a stove at 37° C. overnight.

1.9.2 Transformation of *A. tumefaciens*

Strains C58C1 and AGLO were transformed with the binary plasmids. Briefly, 1 μg of DNA (binary plasmids) was added to a 200-μl aliquot of said competent cells, without thawing, and they were incubated for 5 minutes at 37° C., and immediately thereafter they were incubated at 4° C. for 30 minutes. Subsequently, 1 ml of LB was added and it was cultured at 28° C. for 3-4 hours. Following centrifugation, they were plated in LB medium with kanamycin-rifampycin. The plates were incubated at 28° C. and the colonies appeared approximately 48 hours later. Subsequently, they were cultured and used for the infiltration of *A. thaliana* plants.

1.10 Obtainment of the scFv (APCH1) from Hybridoma 1F12

In order to obtain the sequence corresponding to the scFv (APCH1), we started from hybridoma 1F12 (as indicated in the Materials, section 1.5). The total RNA in the hybridoma cells was isolated using the "Tripure" commercial kit from Roche and the cDNA of the hybridoma that expressed monoclonal antibody 1F12 was obtained by means of RT-PCR using AMV-RT polymerase [Promega]. Subsequently, a first PCR was performed with specific primers for the different variable domains of the immunoglobulins. PCR amplification was performed separately, using two sets of primers that specifically hybridised to the ends of the variable regions of the heavy and light chains.

The following primers were used in the first PCR:

| Name of the primer | Sequence |
|---|---|
| 5' VH.1a | SEQ ID NO: 10 |
| 5' VH.1b | SEQ ID NO: 11 |
| 5' VH.1c | SEQ ID NO: 12 |
| 3' VH.1 | SEQ ID NO: 13 |
| 5' VL1a | SEQ ID NO: 14 |
| 5' VL.1b | SEQ ID NO: 15 |
| 5' VL.1c | SEQ ID NO: 16 |
| 5' VL.1d | SEQ ID NO: 17 |
| 3' VL.1 | SEQ ID NO: 18 |

VH and VL: specific primers for the variable domains of the heavy and light chains of the immunoglobulins.

3 PCRs were performed in order to obtain the variable region of the heavy chain (VH) (5'VH1a.1b.1c with 3'VH1) and 4 were performed in order to obtain the variable region of the light chain (VL). The sequences of the different domains were amplified, as expected, in one of the PCR mixtures for each domain. These amplified sequences (VH and VL) were directly cloned in the pGEM-Teasy cloning plasmid for PCR products, and sub-cloning plasmids pGEM VH and pGEM VL were obtained, which, following the sequencing thereof, were used as templates in a second PCR. In this second PCR, they were amplified with previously designed primers, both domains being bound to an artificial flexible sequence (linker). Therefore, the VH is bound to the linker at its 3'-region and the VL is bound to this sequence at its 5'-region (VH3' linker and VL5' linker) (Table 1). Therefore, since both domains have the overlapping artificial sequence, after several amplification cycles of both sequences, a third PCR was performed in order to obtain both domains bound to an artificial flexible sequence. Therefore, APCH1 contains the variable region of the heavy chain fused, by means of a flexible peptide, to the variable region of the light chain of monoclonal antibody 1F12. Once the APCH1 sequence was amplified by PCR with the specific primers (VH5' xbal and VL3') (Table 1), it was cloned in the cloning plasmid for PCR products, pGEM-Teasy, and sub-cloning plasmid pGEM-APCH1 was obtained. APCH1 was designed so as to add several restriction sequences at the VL3'-end in order to be able to perform the different fusions to the antigens to be assayed, and it contains the XbaI sequence at the VH5'-end, which makes it possible to easily extract fusions from pGEM and take them to the plant transformation plasmids.

1.11 Obtainment of Plasmid pBI APCH1-2L21

Following the sequencing of plasmid pGEM-APCH1 and verification of the integrity thereof, antigen 2L21 of CPV fused to the 3'-region of scFv APCH1 was cloned. To this end, the sequence of peptide 2L21 was amplified by PCR, with primers 2L21XhoI and 2L21SmaI (Table 1), and it was cloned in pGEM for the sequencing thereof. After verifying the sequence, it was extracted by digestion with the XhoI and SmaI enzymes, and introduced, in a directed manner, into plasmid pGEM-APCH1, which had previously been digested with these same enzymes. Following several linkages and transformations, plasmid pGEM APCH1-2L21 was finally obtained, and it was sequenced in order to verify that it correctly maintained the fusion reading frame. Subsequently, this plasmid was digested with the XbaI and SmaI enzymes, in order to extract fusion APCH1-2L21 and introduce it into plasmid pBI-121, which had previously been digested with these same enzymes.

Plasmid pBI-121 contains the β-glucuronidase gene; for this reason, it was digested with the Hind III and SmaI enzymes, and cloned in plasmid p35S TEV with the same enzymes (HindIII-SmaI). Subsequently, the new vector generated (p35S-APCH1-2L21), which contained the 35ScaMV promoter, fusion APCH1-2L21, part of the polylinker (SacI, KpnI) and the Vsp-ter polyadenylation sequence, was digested with the HindIII-EcoRI enzymes, in order to introduce said fusion APCH1-2L21 into the pBI-121 binary plasmid digested with these same enzymes, and plasmid pBI APCH1-2L21 was obtained.

1.12 Genetic Transformation of Plants Mediated by *A. tumefaciens*

The *Agrobacterium* cells previously transformed with the different plant transformation plasmids were grown in 500 ml of LB medium (Sigma), supplemented with kanamycin and rifampycin (Sambrook et al., 1989), for 48 hours at 28° C. Following centrifugation at 3,000 rpm for 20 minutes, the sediment (which contained the bacteria) was re-suspended in 200 ml of infiltration medium: 2.35 g/l of MS (Murashige and Skoog, 1962), 5% of sucrose, 10 g/l of 6-benzylaminopurine and 0.02% of Silweet L-77 (Lehle Seeds, catalogue number VIS-01).

1.12.1 Infiltration of the Flowers

In order to perform the infiltration, plants 6-7 weeks of age, with the greatest possible number of inflorescences, were used. The inflorescences were immersed in the infiltration medium containing *Agrobacterium* in a vacuum chamber, and were subjected to a pressure of 5 kPa (50 mbar) for 10 minutes (Bechtold N. and Pelletier G. *In planta Agrobacterium*-mediated transformation of adult *Arabidopsis thaliana* plants by vacuum infiltration. Methods Mol. Biol. 82: 259-266, 1998). Once the time had elapsed, the vacuum was released as quickly as possible, the plants were washed with water and covered with plastic in order to prevent the desiccation thereof and possible contamination between the different infiltrated plants. Occasionally, plants were infiltrated in the absence of vacuum (Clough S. J. and Bent A. F. Floral dip: a simplified method for *Agrobacterium*-mediated transformation of *Arabidopsis thaliana*. Plant. J. 16: 735-743, 1998). They were kept in culture chambers, under controlled conditions of light, humidity and temperature until the development and maturation of the siliques.

1.12.2 Growth Media and Selection of the Transgenic Plants

The seeds from the previously infiltrated *A. thaliana* plants were sterilised in a solution containing 30% lye and 10% Triton X-100, and were seeded in a Petri dish in GM medium (4.7 g/l MS, 1% sucrose, 0.5 g/l morpholine ethanesulfonic acid (MES), 8 g/l agar and pH 5.7), supplemented with ampicillin and kanamycin (Sambrook et al., 1989).

The T1 seeds were kept at a temperature of 4° C. in the dark for 48 hours and, subsequently, in an in vitro culture chamber, under controlled conditions (16 hours of light and 8 hours in the dark, temperature of 22° C.). After 12-15 days, the transgenic seedlings (capable of growing normally in the presence of kanamycin) were transplanted to soil and taken to culture chambers for the growth and development thereof.

1.13 Analysis of the Transgenic Plants 1.13.1 Isolation of the Total RNA, Quantification, Electrophoresis, Transfer to Membranes The total RNA was purified following the guanidine hydrochloride method described by Logemann et al. (Logemann J., Schell J., and Willmitzer L. Improved method for the isolation of RNA from plant tissues. Anal. Biochem. 163: 16-20, 1987). The quantification of RNA was performed by spectrophotometry.

For the transfer to membranes, the RNA was resolved on 1.5% horizontal agarose gels in the presence of formaldehyde/formamide (Sambrook et al., 1989). The RNA samples were loaded with ethidium bromide in order to visualise them by fluorescence and thereby verify the integrity thereof. Subsequently, the RNA was transferred to Hybond N+ membranes (Amersham) using 0.05 M sodium hydroxide by conventional methods (Sambrook et al., 1989).

1.13.2 Radioactive Labelling of Probes and Hybridisation of Nucleic Acids

All the DNA probes were labelled with 50 μCi of $\alpha^{32}$P-dCTP (Amersham or ICN) by means of the random primer extension method, using the Oligolabelling kit (Pharmacia Biotech). The non-incorporated nucleotides were eliminated by molecular exclusion chromatography in S-200 columns (Pharmacia Biotech), following the manufacturer's instructions. The different DNA fragments used as probes (complete sequences of the fusion genes), as well as the method used to obtain them, are shown in detail below.

TABLE 3

| Probe | Size | Obtainment method | Use |
|---|---|---|---|
| 2L21-GUS | 1.8 kb (approx.) | PCR and digestion | N/S |
| APCH1-2L21 | 0.8 kb (approx.) | Digestion | N |

* N, Northern Blot; S, Southern Blot

The nucleic acid hybridisations were performed in glass tubes containing 10-15 ml of pre-hybridisation solution. The membranes were pre-hybridised for, at least, two hours at the hybridisation temperature. Once this time had elapsed, the denatured radioactively labelled probe was added and the membranes were kept in this solution for 16 to 20 hours.

The low-stringency Southern-type hybridisations were performed in a pre-hybridisation solution with 5×SSPE (0.15 M NaCl, 10 mM NaH$_2$PO$_4$, 1 mM EDTA Na$_2$), 5×Denhardt's Solution (0.02% Ficoll, 0.02% polyvinylpyrrolidone, 0.02% bovine serum albumin, 0.5% sodium dodecyl sulfate (SDS) and 0.5 mg/ml denatured herring sperm DNA). The hybridisation was performed at 65° C. Following the hybridisation, the membranes were subjected to successive washings with 5×SSPE and 0.5% SDS, the salt concentration decreasing with each washing.

The Northern-type hybridisations were performed at 42° C. in 0.25 M phosphate buffer, pH 7.2, 0.25 M NaCl, 1 mM EDTA, 7% SDS, 10% PEG 6000, 40% formamide and 0.2 mg/ml denatured herring sperm DNA. Following the hybridisation, the membranes were subjected to successive washings with 5×SSPE and 0.5% SDS, at 65° C. Each washing lasted approximately 20 minutes. Occasionally, it was necessary to wash with 0.5% SDS.

The membranes were exposed to autoradiographic film (Hyperfilm MP, Amersham) and intensifying screens, at −80° C., for the necessary time to visualise the hybridisation bands. In order to re-use the membranes, these were de-hybridised with a boiling 5% SDS solution, with stirring until cooling of the solution. In order to verify that no radioactivity remained in the membrane, the filters were exposed to autoradiographic film for several days.

1.14 Analysis of Recombinant Proteins Produced in Transgenic Plants 1.14.1 Obtainment of the Total Soluble Protein Fresh vegetable material, generally obtained from the plants' basal rosette leaves, was homogenised in protein extraction buffer (10 mM Tris, pH 7.5, 500 mM NaCl, 0.1% Triton x-100, 1% β-mercaptoethanol and 1 mM PMFS as a protease inhibitor), after being cut and introduced in 1.5-ml Eppendorf tubes and kept in ice (4° C.). Following homogenisation, they were centrifuged for 10-15 minutes at 13,000 rpm, and the supernatant was collected. In some cases, frozen material was used. In order to solubilise some of the precipitated proteins and improve the extraction yields, a buffer containing urea was used. The protein analysis was performed in acrylamide-bisacrylamide electrophoresis gels (30:1) in the presence of SDS.

1.14.2 Electrophoresis in Polyacrylamide-Glycine Gels in the Presence of SDS

Protein electrophoresis under denaturing conditions was performed in discontinuous acrylamide-bisacrylamide gels in the presence of SDS, following the conventional method (Sambrook et al., 1989). Acrylamide-bisacrylamide separating gels were prepared (Biorad or Serva), at variable concentrations between 7% and 15%, depending on the expected molecular weight of the protein to be analysed, jointly with thickening gels with a 3.5% concentration of acrylamide-bisacrylamide (Sambrook et al., 1989). The electrophoreses were developed at a constant voltage of between 100 and 140 V in the case of minigels (7×9 cm).

All the samples were quantified following the separation thereof by electrophoresis, in accordance with the Bradford-Lowry method (Biorad protein assay). They were solubilised in protein dissociation buffer (0.5 M Tris, pH 8.0, 10% SDS, glycerol, β-mercaptoethanol, 0.02% bromophenol blue), heated for 5 minutes at 100° C. and subsequently applied to the gel.

1.14.3 Transfer of Proteins to Nitrocelullose Filters

The transfer of proteins to nitrocellulose filters (Bio-Rad 2) was performed in a humid cuvette at a constant voltage of 100 V for 1 hour, or by semi-dry transfer (Bio-Rad) for 25 minutes at 20 volts. In both cases, the same transfer buffer was used (25 mM Tris, 151.8 mM glycine and 20% methanol (v/v)).

1.14.4 Ponceau Red Staining of Proteins Transferred to Nitrocellulose

Once the proteins were transferred to the nitrocellulose filters, the latter were stained, in order to check the integrity thereof, with a 0.2% Ponceau solution (Sigma) in 30% trichloroacetic acid (p/v) and 30% sulfosalicylic acid (p/v) for 1 minute by immersion. Subsequently, they were washed with distilled water in order to eliminate the excess colouring agent.

1.14.5 Protein Analysis by Immunoblotting or Western Blotting

Once the proteins were transferred and immobilised on nitrocellulose filters, said nitrocellulose filters were blocked at 37° C. for 1 hour with 2% powder skim milk (p/v) in PBS, or overnight at 4° C. under stirring, with the same blocking solution. Subsequently, the filters were incubated for 1 hour with the specific antibody diluted in 0.05% PBS-Tween 20 (v/v) at the adequate concentration for each assay. The filters were washed 3 times for 10 minutes in washing buffer (PBS 1×-Tween) each time and incubated in the same dilution solution with the corresponding secondary antibody, at ambient temperature for 1 hour. After repeating the washings, the development was performed using the adequate substrate on the basis of the conjugation of the secondary antibody (NBT-BCIP (Roche), ECL (Amersham)).

1.15 Immunogenic Analysis of the Proteins Expressed in Plants 1.15.1 Obtainment of the Sera The sera were obtained by incubation of the blood at 37° C. for 30 minutes, followed by a 14-hour-long incubation at 4° C. The blood clots were separated and the sera were clarified by centrifugation at 1,500 rpm for 10 minutes.

1.15.2 Detection of Antibodies by ELISA

The ELISA plate wells were lined with 0.2 μg of peptide 2L21 per well, diluted in binding buffer (carbonate/bicarbonate), at 4° C. for 12 hours. It was blocked with a solution of 0.05% PBS-Tween-20 (v/v) and 5% fetal bovine serum or BSA, at 37° C. for 1 hour under stirring. After washing 3 times with a 0.05% PBS-Tween 20 solution, the sera to be determined were incubated at different dilutions in 0.05% PBS-Tween 20, at 37° C. for 1 hour, under stirring. After 5 washings with PBS-Tween, the wells were incubated with a 0.05% PBS-Tween-20 solution which contained peroxidase-conjugated anti-mouse (Amersham) at a dilution of 1/500, at 37° C. for 1 hour, under stirring. The plates were washed and developed using or-phenylenediamine (OPD) (Sigma-Aldrich) as the substrate, prepared in water containing 0.1% hydrogen peroxide. The reactions were stopped with 3 N sulfuric acid and, subsequently, the absorbance of each plate well was read in an ELISA reader at a wavelength of 492 nm.

In order to detect antibodies against the canine parvovirus capsid, the INGEZIM PARVO CANINO 1.5.CPV.K.1 Kit (Ingenasa) was used, which is designed for the detection and quantification of specific antibodies against canine parvovirus in dog sera.

In order to determine the title of antibodies in the sera analysed by ELISA, serial dilutions of the sera to be titrated were performed, expressing the title of each serum as the inverse of the maximum dilution of said serum wherein the absorbance at 492 nm was significantly greater than that of the negative controls (2 times greater).

1.15.3 Characterisation of Antibodies by Immunoblotting

The antigen specificity of the antibodies obtained from the immunised animals was determined by means of immunoblotting. The protein of the VP2 capsid produced in baculovirus (Ingenasa) was re-suspended in protein dissociation buffer, boiled for 5 minutes and loaded in polyacrylamide-glycine gel in the presence of SDS and transferred to a nitrocellulose membrane (Biorad). The mouse sera were tested at a limit dilution from 1/10, and the anti-mouse secondary antibody was conjugated with alkaline phosphatase (Roche). The substrate used for the reaction was nitroblue-tetrazolium-4-chloro-3-indolphosphate (NBT-BCIP, Roche).

1.16 Experimental Models and Immunisations 1.16.1 Inoculations of Mice with Plant Extracts by Intraperitoneal Route Female mice of the Swiss stock, 11 weeks of age, were immunised, by intraperitoneal route, on days 0, 7 and 14, with plant extracts that expressed the recombinant protein under study (APCH1-2L21) (3 mg of total soluble protein/dose). Freund's complete adjuvant (Sigma) was used for the first inoculation and Freund's incomplete adjuvant (Sigma) was used for the rest.

The control mice were immunised, using the same protocol, with untransformed plant extracts or plant extracts transformed with the vector without the transgene. Ten days after the last immunisation, the mice were bled and the sera were obtained in order to be studied.

Figure 1:
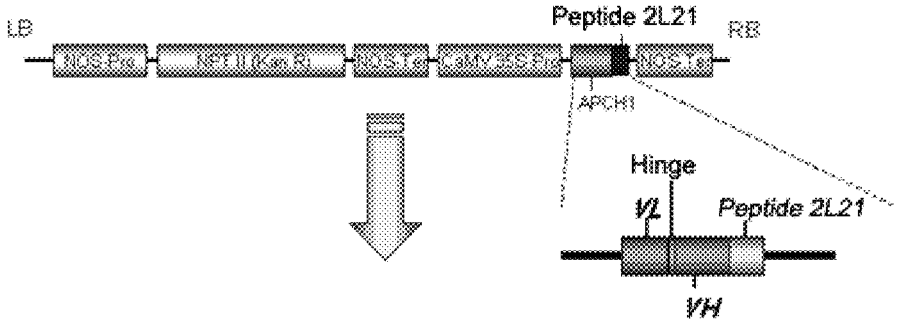
FIG. 1 is a schematic view of the gene expression construct of plasmid pBI APCH1-2L21.
Figure 1:
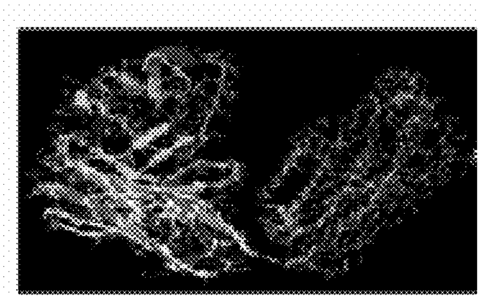

1.17 Obtainment of the Single-Chain Recombinant APCH1 Antibody Fused to Peptide 2L21 and the Expression Thereof in Transgenic Plants The obtainment of the single-chain recombinant antibody (scFv) called APCH1 in this description was performed by means of PCR amplifications from mRNAs, starting from hybridoma 1F12, and subsequent molecular clonings, as described in the section on Materials and Methods. The final construct is composed of the variable domain of the heavy chain (VH) with the native signal peptide of antibody 1F12, the variable domain of the light chain (VL) wherefrom the signal peptide and an artificial flexible peptide that binds them has been eliminated. Following sequencing of the resulting chimeric gene and verification of the integrity thereof, antigen 2L21 of CPV fused to the 3'-region of APCH1 was cloned. To this end, the sequence of antigen 2L21 was amplified by PCR, with the specific primers that make it possible to keep the fusion reading frame open. Following several subclonings, this fragment was introduced into binary plasmid pBI 121, leading to plasmid pBI APCH1-2L21, which contains the 35S constitutive promoter; the latter directs the expression of the sequence corresponding to the fusion protein and the polyadenylation sequence of the Nos gene of *Agrobacterium* (FIG. 1). This plasmid was introduced into *Agrobacterium tumefaciens*, wherewith *Arabidopsis thaliana* plants were transformed by means of floral infiltration (Clough, S. J. and Bent, A. F. 1998. Floral dip: a simplified method for *Agrobacterium*-mediated transformation of *Arabidopsis thaliana*. Plant J. 16: 735-743).

1.18 Analysis of the Expression of the Fusion Antigen (APCH1-2L21) in the Transgenic Plants Obtained Following transformation of the plants, multiple transgenic lines with a phenotype similar to the wild one were obtained. Subsequently, approximately 30 independent transgenic lines were analysed in order to determine the expression of the transgene and the accumulation of the fusion protein (APCH1-2L21). Previously, different scFv have been expressed in plants with different objectives, and a great variation in the expression and accumulation levels of these molecules has been obtained (Fiedler, U. and Conrad, U. 1995. High-level production and long-term storage of engineered antibodies in transgenic tobacco seeds. Biotechnology (N.Y.) 13: 1090-1093). Therefore, the first step was to study the correct transcription of the transgene in order to subsequently analyse the accumulation levels of the fusion protein.

The total RNA of the different lines was obtained from fresh leaves of plants transformed with this construct, separating the different RNAs in agarose-formamide gels, and subsequently transferring the latter to nitrocellulose filters in order to be analysed. The Northern blots performed on these filters, using the complete fusion sequence (APCH1-2L21) as a probe, showed that some transgenic lines exhibited a very intense hybridisation band of the size expected for the mRNA corresponding to the fusion protein (FIG. 2).

Subsequently, in order to verify the correct translation and accumulation of the recombinant protein in plant cells, 12% SDS-PAGE gels were performed with total soluble protein extracts from these lines. To this end, monoclonal antibody 3C9 (Ingenasa), specific for peptide 2L21, was used in the Western Blot analyses. These analyses showed the presence of a band of approximately 32 kDa, corresponding to the APCH1-2L21 protein, in the extracts from the lines that exhibited the highest messenger accumulation levels.

Figure 2:
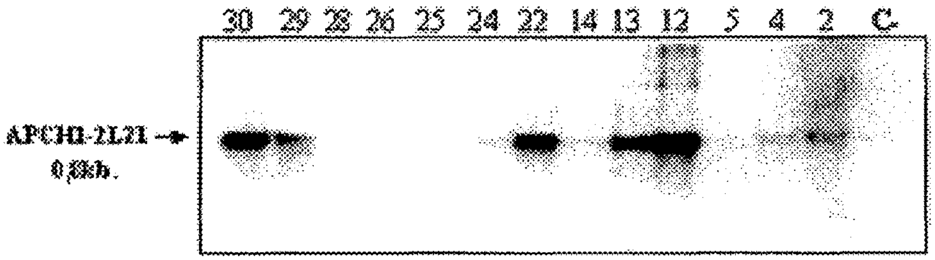
FIG. 2 illustrates the analysis of the expression of antigen 2L21 fused to scFv APCH1 in some lines that express said fusion protein (APCH1-2L21).
Figure 2:
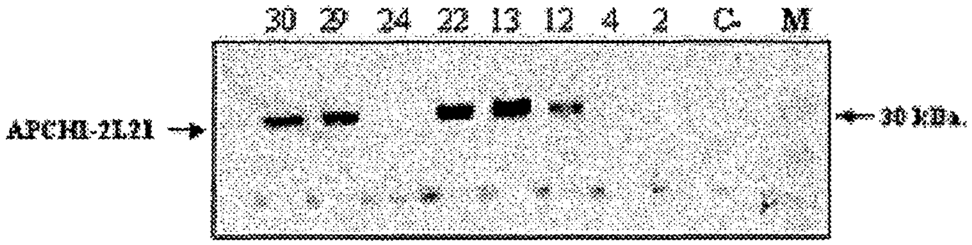

As may be observed in FIG. 2, there is a positive correlation between the transcription levels detected and the protein in the lines analysed, such that those plants with the highest mRNA levels exhibited a greater accumulation of this protein. The predicted three-dimensional structure of APCH1-2L21 indicates that it is a globular protein, not a multimeric one (FIG. 1C). These results indicate that there are no obstacles for the transcription and translation of this fusion protein in the cytoplasm of *A. thaliana* cells.

1.19 Analysis of the Binding Capacity to its Target Antigen in the Antigen-Presenting Cells of the Recombinant Antibody Fused to the Vaccine Peptide (APCH1-2L21)

In order to verify that fusion protein APCH1-2L21 produced in plants maintained the antigen recognition characteristics of the original 1F12 antibody, fluorescence and immunohistochemical assays were performed using porcine alveolar macrophages, which have a large number of these receptors (class-II SLA-DR).

For these assays, alveolar macrophages, previously fixed with 1 μg of soluble protein newly extracted from plants transformed with plasmid pBI APCH1-2L21, were incubated overnight at 4° C. Subsequently, after washing the macrophages with PBS-Tween in order to eliminate unspecific bonds, a second incubation was performed with specific antibody 3C9 against epitope 2L21. Subsequently, the immuno-complex was developed in two different ways. For immunofluorescence, an Alexa-Fluor™488-conjugated goat anti-mouse antibody (Molecular Probes) was used, which labels in green. In the case of labelling with peroxidase, a peroxidase-conjugated sheep anti-mouse antibody (Amersham Pharmacia) was used, which labels in brown. As a negative control, macrophages were incubated in parallel with plant extracts transformed with plasmid pBI-TEV Vp60, under the same conditions, and supernatant (10 μg) of the hybridoma that expresses antibody 1F12 was used as a positive control.

Figure 3:
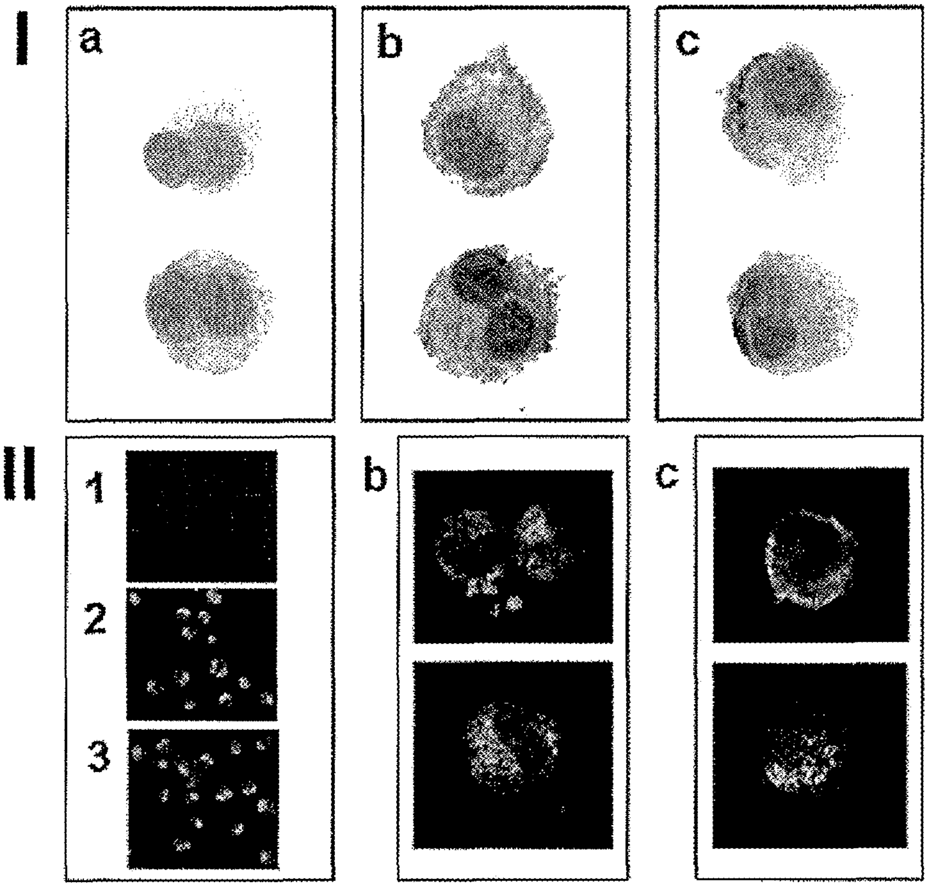
FIG. 3 shows the result of the specific labelling of the surface of porcine alveolar macrophages with peroxidase (I) and with fluorescent labelling (II).

As a result of this experiment, labelling was only obtained in the macrophages incubated with the supernatant of hybridoma 1F12 and in the plant extracts that expressed APCH1-2L21, whereas no signals appeared in the negative control. A specific labelling pattern was found on the surface of the macrophages with both conjugates, which was very similar in the cells treated with the supernatant of the hybridoma and in the plant extracts that expressed APCH1-2L21 (FIG. 3).

These results confirm the functionality and activity of fusion protein APCH1-2L21 expressed in plants, which maintains its specificity for class-II SLA-DR molecules of porcine alveolar macrophages.

1.20 Study of the Increase in Immunogenicity Conferred to Peptide 2L21 by Antibody APCH1

In order to evaluate the efficacy of the immune-response-enhancing molecule provided by this invention, 5 female mice of the Swiss stock, 11 weeks of age, were immunised with immunogen, by intraperitoneal route, on days 0, 7 and 14, with plant extracts (3 mg of total soluble protein/dose) that expressed the recombinant protein under study, the same peptide 2L21 fused to an irrelevant protein (β-GUS), or with 100 μg of synthetic peptide 2L21. Freund's complete adjuvant (SIGMA) was used for the first inoculation and Freund's incomplete adjuvant (SIGMA) was used for the rest. Ten days after the last immunisation, the mice were bled and the sera were obtained in order to be studied.

As a result of this study, the peptide fused to the antibody induced titles of antibodies in the mice that were 600 times greater than those obtained with the peptide alone and over 50 times greater than those obtained with the peptide fused to an irrelevant protein (FIG. 4). These data confirm the hypothesis of the increase in the immunogenicity of a peptide through the directioning thereof toward antigen-presenting cells by means of antibody APCH1. Furthermore, comparative experiments of the immunogenicity of this peptide fused to protein KLH, a habitual carrier for peptide vaccines, and fused to antibody APCH1 showed that directioning of the antigen toward the antibody generated a number of antibody molecules per peptide molecule that was 26 times greater.

Example 2

Directioning of Vaccinal Antigens Toward Antigen-Presenting Cells for Immune Response Enhancement in Animals. Fusion of the Single-Chain Recombinant APCH1 Antibody to Protein E2T of the Bovine Viral Diarrhoea Virus and the Expression Thereof in Mammalian Cells 2.1 Cells Mammalian CHO-K1 cells (ovarian cells) free from adventitious viruses, obtained from the Cell Culture section of the Institute of Virology (PVA76/04), were used. Mammalian CHOK1 (Chinese Hamster Ovary cells) cells were used.

2.2 Strains of *Escherichia coli* Used

DH5-α strains of *Escherichia coli* (Clontech), which present the following characteristics, were used for the transformation and growth of the plasmids:

Bacterial strain: DH5-α

Genotype: supE44 hsd R17 recA1 endA1 gyrA96 thi-1 relA1

Remarkable units: Strain deficient in recombination, used for plating and growth of plasmids.

2.3 Plasmids Used 2.3.1 Commercial Plasmids

In order to obtain the different constructs that expressed the different peptides assayed, various commercial plasmids were used. Plasmid pGEM-Teasy was used for the cloning and sequencing of PCR products, whereas plasmid pcDNA 3.1 was used for the generation of the stable mammalian line:

- pGEM-Teasy (Promega): this plasmid is especially designed for the cloning and sequencing of PCR products. It contains a region with multiple restriction sites (polylinker). The polylinker has been previously digested with EcoRV and, subsequently, 3'-thymidines have been added at both ends in order to facilitate the cloning of the PCR products. Moreover, it makes it possible to select the recombinants by means of the LacZ gene.
- pcDNA 3.1 (Invitrogen): this plasmid is derived from pcDNA3 and was designed for the transient, stable expression in mammalian cells. The vector contains the following elements.

2.3.2 Mammalian Cell Transformation Plasmids Developed During the Implementation of this Invention For the embodiment of this example, the plasmid identified as pcDNA APCH1-E2T was generated, which was used in the transformation of the CHOK-1 cells. The antigen expressed in said plasmid comes from the fusion of APCH1 with secretory protein E2, without its transmembrane domain (E2T), of the Bovine Viral Diarrhoea Virus (VDVB).

The sequences that encode said antigen and the respective fusions thereof were obtained by PCR amplification. The primers used are listed in the following table:

| Name of the primer | 5'-3' sequence |
|---|---|
| P1 XmaI | SEQ ID NO: 19 |
| P3 SpeI | SEQ ID NO: 20 |

Positions 2-7 of SEQ ID NO: 19 are the restriction targets.

In order to detect the recombinant protein produced in the supernatant of mammalian cells, a commercial mouse monoclonal antibody and a rabbit polyclonal serum specifically developed for this purpose, and the respective secondary antibodies conjugated to alkaline phosphatase (AP) and/or peroxidase (HRP), were used:

| Monoclonal antibody (mouse) | Specificity | Use | Supplier |
|---|---|---|---|
| 2.9H | anti-E2 VDVB | WB/ELISA | CEVAN |
| C3A | Anti-E2 VDVB | WB | BOMELLI |
| **Polyclonal antibody (rabbit)** | **Specificity** | **Use** | **Supplier** |
| IgG | anti-E2T | ELISA | Lab C (IV-INTA) |

| Secondary antibodies-conjugated | Supplier |
|---|---|
| Anti-mouse conjugated with AP | KPL |
| Anti-mouse conjugated with HRP | KPL |

2.4 Transfection of the CHOK 1 Cell Line

In order to obtain the stable line, the transfection method previously standardised in the laboratory was used.

Lines transfected in a stable manner were obtained. To this end, T-75 flasks with monolayers of CHO-K1 were transfected with lipofectamine at an 80% confluence. A monolayer of cells was transfected with pcDNA E2T and pcDNAAPCH1-E2T with a vector of the same series of pcDNA 3.1 (Invitrogen) that contained the LacZ gene, in order to use this line to more easily check the evolution and development of the stable lines. At 24 h post-transfection, a sub-culture of the transfected cells was performed in four T-75s and the selection process was initiated by adding the antibiotic geneticin (Invitrogen) at a concentration of 700 μg/ml to the culture medium. At 14 days of culture, the presence of cell foci resistant to the selected antibiotic was evident. At that time, a new sub-culture of cells was performed and a first isolation round of individual cells by limit dilution was initiated in 96-well plates. At 21 days of culture, the foci were once again observed and a new round of limit dilution was initiated in order to isolate individual clones. The limit dilution process was repeated twice for each round. The highest dilutions that gave positive by Western Blot for the expression of the recombinant proteins were used in the second limit dilution process. Finally, the positive clones were amplified and frozen in liquid nitrogen for storage (FIG. 5).

2.5. Detection of the Recombinant Protein in the Cell Lines Developed 2.5.1 Electrophoresis in Polyacrylamide Gels (PAGE)

Electrophoresis in polyacrylamide gel under denaturing conditions (SDS-PAGE) was performed in accordance with the method described by Laemmli U.K., using the discontinuous gel system in a Mini Protean II equipment (Bio-Rad). The latter is composed of a stacking gel with a 1.7% concentration of polyacrylamide (m/v), and a separating gel, with an 8% concentration of polyacrylamide (m/v). The samples were pre-incubated with seeding buffer (12.5% Tris-HCl buffer v/v (pH 6.8), 10% glycerol v/v, 2% SDS m/v, 5% β-mercaptoethanol v/v, 0.2% bromophenol blue m/v) for 5 minutes in a boiling water bath. Once the seeding was performed, the electrophoretic separation was performed in 1× running buffer (5× running buffer: 1.5% Tris base m/v, 7.2% glycine m/v, 0.5% SDS m/v), applying a constant voltage of 100 V for 4 hours.

2.5.2 Western Blot

Once the electrophoretic separation was concluded, electrotransfer on PVDF membranes with a 0.45-μm pore size (Immobilon Transfer Membrana-Millipore) was performed. It was performed for 60 min at 20 V in a Mini Protean II equipment (Bio-Rad) containing 1× transfer solution (25 mM Tris Base, 192 mM glycine, 0.15% SDS v/v, 20% methanol v/v). Once the transfer was concluded, the membrane surface was blocked with blocking solution (3% powder skim milk (Molico) m/v in 0.05% PBS 1×-Tween buffer v/v) at 37° C. for 1 h. Subsequently, it was incubated O.N. at 4° C. with an anti-E2 monoclonal antibody (CA3-Bommelli) conveniently diluted in blocking solution. Subsequently, it was incubated with a peroxidase-conjugated mouse anti-IgG monoclonal antibody (KPL) conveniently diluted in blocking solution at ambient temperature for 1 h. Following the incubations, 3 washings in 0.05% PBS 1×-Tween v/v were performed, for 10 min each.

The membrane was incubated with the substrate of the peroxidase enzyme; the commercial Western Lighting Chemiluminescence Reagent Plus kit (Perkin Elmer LAS, Inc.) was used, following the manufacturer's recommendations.

Finally, the membrane was exposed in photosensitive plates (Hyperfilm-Amersham Biosciences) and subsequently developed in radiographic developer solution (G 150 Agfa); it was later rinsed in 2% acetic acid v/v and, finally, fixed in radiographic fixative solution (G 334 Agfa).

2.5.3 Staining with Coomassie

Once the electrophoretic running was concluded, the gel was subjected to staining with 0.1% m/v Coomassie Bright Blue R-250 (Sigma) in a mixture of methanol:acetic acid:water (40:10:50). In order to destain the gels, a destaining solution (methanol:acetic acid:water; 5.0:7.5:87.5, respectively) was used. The destaining was performed under stirring at ambient temperature.

2.5.4 ELISA Sandwich for the Detection of APCH1-E2T and E2T from Cell Culture Supernatant Maxisorp plates (NUNC) were sensitised with monoclonal antibody 2.9H, adequately diluted in carbonate-bicarbonate buffer (1.59 g/l $Na_2CO_3$, 2.93 g/l $NaHCO_3$) O.N. at 4° C. Subsequently, the plate was blocked with blocking solution (0.1% PBS 1×-Tween 20 v/v; 1% skim milk m/v), incubating it at 37° C. for 1 h. Subsequently, the samples to be analysed were incorporated (supernatant of CHO-K1-APCH1-E2T or E2T cells), incubating the plates at 37° C. for 1 h. It was washed 5 times and incubated at 37° C. for 1 h with a rabbit polyclonal serum against glycoprotein E2, in the adequate dilution. It was once again washed 5 times and, finally, a peroxidase-conjugated rabbit anti-IgG monoclonal antibody (KPL), adequately diluted, was incorporated, incubating it at 37° C. for 40 minutes. It was washed 5 times and the peroxidase substrate (0.55 mg/ml ABTS, 0.015% $H_2O_2$, citrate buffer (pH: 5)) was placed. The reaction was stopped with 5% SDS m/v. Reading of the plates was performed at 405 nm (ELISA reader, Multiskan Ex, Labsystems Inc). The dilutions were performed in blocking solution, the washings were made with PBS 1× and a volume of 50 μl per well was used.

2.6 Purification of the E2T from CHOK1 APCH1-E2T and CHOK1 E2T Cell Superanatant Once the monolayer was formed (usually 72 h), the supernatant was harvested, PMSF at a final concentration of 1 mM was added, and it was preserved at −20° C. until it was to be used.

The supernatant was thawed and the ionic strength thereof was increased with the 10× binding-washing solution (3 M NaCl, 0.5 M $NaHPO_4$). 20 mM Imidazole was added and the pH was taken to 8 with 10 N NaOH.

On the other hand, the nickel was equilibrated with the 1× binding-washing solution (0.3 M NaCl, 0.05 M $NaHPO_4$) with 20 mM Imidazole, and incubated under stirring for 30 minutes at 4° C. It was centrifuged at 2,500 g for 5 minutes, the supernatant was discarded and the nickel was incubated with the supernatant O.N. at 4° C. under stirring.

It was centrifuged at 2,500 g for 3 minutes, the supernatant was discarded and it was washed with the 1× binding-washing solution, adding 13 mM Imidazole, 1 mM PMSF, 1 mM leupeptin at 4° C. for 15 minutes, until the supernatant absorbance at 280 nm was low and constant.

Finally, the elution was performed with elution solution (1× binding-washing solution with 200 mM Imidazole, 1 mM PMSF, 1 mM leupeptin), incubating it at 4° C. for 15 minutes under stirring. It was centrifuged at 2,500 rpm for 3 minutes and the supernatant was recovered.

2.7 Immunogenic Analysis of the Proteins Expressed in Plants 2.7.1 Immunisation of Guinea Pigs 200-300-g guinea pigs from the AL II strain, supplied by the Biotery of the Research Center in Veterinary and Agronomic Sciences (CICVyA), INTA (National Institute for Agricultural Technology) Castelar. Two 1-ml doses of oily vaccine (aqueous: oily, 40%:60%) were inoculated on day 0 and 30 by intramuscular route (500 µl for each hind leg).

Prior to each inoculation, the animals were bled by cardiac puncture, extracting 3 ml of blood per animal. It was incubated at 37° C. for 1 h and at 4° C. for 30 minutes. The serum was extracted by centrifugation at 1,000 g for 15 minutes, aliquoted and preserved at −20° C. until it was to be used.

During the experimentation, the animals were kept in groups of four in 1-$m^2$ cages, which were kept in an enclosure isolated from the exterior, under a ventilated atmosphere. The cage beds and the water were periodically changed.

2.7.2 Immunisation of Bovines

Sero-negative, non-infected bovines from the INTA were used, which had been previously tested to verify their health condition by means of ELISA, SN and PCR.

The bovines were immunised with two doses of the vaccine to be assayed, one at the initial time and the other at 30 days post-primo-vaccination. The immunisation was performed by intramuscular route. The inoculum volume was 5 ml. Blood samples were taken every seven days post-vaccination for the subsequent analysis of antibodies in serum.

2.7.3 Obtainment of the Sera

The sera were obtained by incubation of the blood at 37° C. for 30 minutes, followed by a 14-hour-long incubation at 4° C. The blood clots were separated and the sera were clarified by centrifugation at 1,500 rpm for 10 minutes.

2.7.4 Viral Seroneutralisation (SN)

The level of neutralising antibodies (NA) was determined following Howard et al.'s protocol (1987).

2.7.5 Detection of Antibodies by ELISA

The level of antibodies was determined using a slightly modified assay based on the ELISA developed by Marzocca et al. (2007).

2.8 Production of Protein APCH1 E2T and E2T in the CHOK 1 Cells

The selected clones were grown in MEM-E medium (Gibco); 10% SFB (Quiroga) and 1% antibiotic (penicillin; streptomycin; gentamycin). In order to evaluate the production of the recombinant proteins in the supernatant of the cell lines developed, the latter were grown in T75 flasks (FIG. 6A) and in rollers (FIG. 6B). In each culture, the secretion kinetics of the recombinant protein were studied. The assays were performed in duplicate for each of the T75 groups with and without DMSO, and the roller groups with and without DMSO. In the case of the T75, $3\times10^6$ cells were seeded at time 0, whereas the rollers were initiated with $16\times10^6$ cells, in order to maintain the ratio of cells per volume between the two. 1 ml was extracted every 24 h and they were preserved at −20° C. until the ELISA was performed.

2.9 Purification of APCH1E2T and E2T by Metal Chelate Chromatography (IMAC):

Using the protocol described in point 2.3, protein APCH1-E2T was obtained with a high degree of purity and the appearance of a single band for E2T and of three bands for APCH1-E2T was recorded; the heaviest band pertained to the fusion protein, the intermediate band probably pertained to traces of BSA, and the lightest one is a product of the proteolysis of APCH1-E2T (confirmed by Western Blot). The approximate yield of the entire process was of the order of 100 µg of purified protein for every 1 liter of supernatant (FIG. 7).

2.10 Recognition of APCH1-E2T Toward MHC Class-II Peripheral-Blood Mononuclear Cells (PBMCs) from Different Species PBMCs were purified from heparinised blood from different animals (bovine, pig, horse, goat and sheep) with Ficoll-Hypaque (Amersham). The cells obtained in this manner were subsequently incubated with PBS (isotype control), E2T or APCH1-E2T, and later labelled with a mouse anti-E2 monoclonal antibody (VDVB, strain NADL) and a phycoerythrin-coupled mouse anti-IgG monoclonal antibody. The labelled cells were analysed in a flow cytometer, and the results were reported as the percentage of positive cells, which were those cells that had a fluorescence intensity within an intensity range outside that of the label pertaining to the isotype control. In all the species analysed, the binding of APCH1-E2T was significantly greater than that obtained for E2T.

2.11 Study of the Increase in Immunogenicity Conferred to Protein E2T by Antibody APCH1

In order to evaluate the efficacy of the immune-response-enhancing molecule provided by this invention, assays were performed in an experimental model (guinea pigs) and in bovines (final target for which fusion molecule APCH1-E2T was developed).

2.11.1 Assays in Guinea Pigs

The experimental groups used to evaluate the APCH1-E2T molecule are shown in table 2. As may be observed, protein E2T fused to the antibody induced titles of neutralising antibodies greater than those obtained with protein E2T in the guinea pigs (FIG. 9). Experimental groups:

| Group | No. of guinea pigs | Dose per animal (µg) |
|---|---|---|
| E2T | 5 | 0.2 |
| APCH1-E2T | 5 | 0.2 |
| Lac Z (−) | 4 | 1 |

2.11.2 Assays in Bovines

Once the enhancement of the immune response in the experimental model of guinea pigs was obtained, the enhancement capacity of the APCH1 molecule in bovines was evaluated. Table 3 shows the experimental groups assayed. With the highest dose (1 μg), no differences were detected between the experimental groups (FIG. 10A); however, with the 0.2-μg dose, protein APCH1-E2T turned out to be more efficient than the protein per se, since it allowed for a specific antibody response (FIG. 10B). Likewise, when the title of antibodies obtained for the 0.2-μg dose was calculated, it was observed that only the APCH1-E2T molecule was capable of inducing specific antibodies (FIG. 10C). Experimental groups:

| Group | No. of bovines | Dose per animal (μg) |
|---|---|---|
| E2T | 3 | 1 |
| E2T | 3 | 0.2 |
| APCH1-E2T | 3 | 1 |
| APCH1-E2T | 3 | 0.2 |
| Lac Z (−) | 3 | 1 |

The invention claimed is:

1. A gene construct comprising, operatively bound, at least:

a) one nucleotide sequence (A) that encodes a polypeptide with SEQ ID NO: 1, which has a region that recognises the β chain of the Class-II DR antigen present on the surface of antigen-presenting cells; and b) one nucleotide sequence (B) that encodes a vaccinal antigen of interest, susceptible to inducing an immune response in the host wherein it is introduced.

2. The gene construct of claim 1, wherein the vaccinal antigen of interest is selected from the group consisting of: peptide 2L21 from the canine parvovirus, protein VP60 from the rabbit haemorrhagic disease virus, protein VP6 from the rotavirus, protein E2 or E2T from the bovine viral diarrhoea virus, and the haemagglutinin protein from the influenza virus.

3. The gene construct of claim 1, wherein said gene construct is pBIAPCH1-2L21 and comprises a nucleotide sequence (A) that encodes SEQ ID NO: 1 and a nucleotide sequence (B) that encodes SEQ ID NO: 21, corresponding to vaccinal antigen 2L21 of the canine parvovirus.

4. The gene construct of claim 1, wherein said gene construct is pcDNAAPCH1-E2T and comprises a nucleotide sequence (A) that encodes SEQ ID NO: 1 and a nucleotide sequence (B) that encodes SEQ ID NO: 23, corresponding to vaccinal antigen E2T of the bovine viral diarrhoea virus.

5. The gene construct of claim 1, wherein said gene construct comprises a nucleic acid sequence (C) that encodes a spacer peptide.

6. The gene construct of claim 5, wherein the spacer peptide is selected from SEQ ID NO: 2 or SEQ ID NO: 3.

7. The gene construct of claim 1, wherein said gene construct comprises a nucleic acid sequence (D) that encodes a peptide susceptible to being used for isolation or purification purposes located downstream from the 3'-end of the nucleotide sequence (B).

8. The gene construct of claim 1, wherein said gene construct comprises promoter sequences, sequences that encode transcriptional regulators, ribosome-binding sequences (RBS) or transcription termination sequences.

9. The gene construct of claim 1, wherein said gene construct comprises a marker selected from antibiotic resistance genes or genes that confer resistance to toxic compounds.

10. A recombinant expression vector, useful to transform, comprising the gene construct of claim 1.

11. The recombinant expression vector of claim 10, wherein the recombinant expression vector is *Agrobacterium tumefaciens*.

12. The recombinant expression vector of claim 10, wherein the recombinant expression vector is a virus.

13. An isolated cell transformed or transfected with a recombinant expression vector, wherein the recombinant expression vector comprises the gene construct of claim 1 in its genome.

14. A transgenic plant transformed or transfected with a recombinant expression vector, wherein the transgenic plant comprises the gene construct of claim 1 in its genome.

15. An isolated transgenic animal cell transformed or transfected with a recombinant expression vector, wherein the transgenic animal cell comprises the gene construct of claim 1 in its genome.

16. A fusion protein encoded by the gene construct of claim 1, wherein said fusion protein is capable of producing an immune response when introduced into a host.

17. The fusion protein of claim 16, wherein the fusion protein is APCH1-2L21 and comprises an amino acid sequence SEQ ID NO: 1 (A) and an amino acid sequence SEQ ID NO: 21 (B), corresponding to vaccinal antigen 2L21 of the canine parvovirus.

18. The fusion protein of claim 16, wherein the fusion protein is APCH1-E2T and comprises an amino acid sequence SEQ ID NO: 1 (A) and an amino acid sequence SEQ ID NO: 23 (B), corresponding to vaccinal antigen E2T of the bovine viral diarrhoea virus.

19. A vaccine that comprises the fusion protein of claim 16 and, optionally, a pharmaceutically acceptable excipient.

20. The recombinant expression vector of claim 12, wherein the virus is *Baculovirus*.

21. A method for the treatment of diseases, the method comprising administering a pharmaceutically acceptable quantity of the vaccine of claim 19 to an individual or to an animal.

22. The method of claim 21, wherein the administration is performed by oral, intramuscular, subcutaneous, intraperitoneal or intravenous route.

* * * * *

UNITED STATES PATENT AND TRADEMARK OFFICE

CERTIFICATE OF CORRECTION

PATENT NO. : 8,557,246 B2
APPLICATION NO. : 12/922287
DATED : October 15, 2013
INVENTOR(S) : José Angel Martínez Escribano et al.

It is certified that error appears in the above-identified patent and that said Letters Patent is hereby corrected as shown below:

In the Claims

Column 38, Line 66: change "10. A recombinant expression vector, useful to transform," to --10. A recombinant expression vector,--

Signed and Sealed this
Seventeenth Day of December, 2013

Margaret A. Focarino
*Commissioner for Patents of the United States Patent and Trademark Office*